United States Patent
Dodds et al.

(10) Patent No.: US 10,265,367 B2
(45) Date of Patent: Apr. 23, 2019

(54) SYNERGISTIC ANTIBACTERIAL EFFECTS OF MAGNOLIA BARK EXTRACT AND L-ARGININE, N-$^{\alpha}$-LAUROYL ETHYL ESTER ON PLAQUE BIOFILM

(71) Applicant: WM. WRIGLEY JR. COMPANY, Chicago, IL (US)

(72) Inventors: Michael W. Dodds, Chicago, IL (US); Minmin Tian, Chicago, IL (US); Taichi Inui, Chicago, IL (US); Lilian Ramirez, Chicago, IL (US); Marcelo B. Aspiras, Chicago, IL (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 0 days.

(21) Appl. No.: 15/757,214

(22) PCT Filed: Sep. 12, 2016

(86) PCT No.: PCT/US2016/051311
§ 371 (c)(1),
(2) Date: Mar. 2, 2018

(87) PCT Pub. No.: WO2017/044948
PCT Pub. Date: Mar. 16, 2017

(65) Prior Publication Data
US 2018/0243359 A1   Aug. 30, 2018

Related U.S. Application Data

(60) Provisional application No. 62/217,213, filed on Sep. 11, 2015.

(51) Int. Cl.

| | | |
|---|---|---|
| A23G 3/36 | (2006.01) | |
| A23G 3/44 | (2006.01) | |
| A23G 3/48 | (2006.01) | |
| A23G 4/06 | (2006.01) | |
| A23G 4/12 | (2006.01) | |
| A23G 4/14 | (2006.01) | |
| A61K 8/44 | (2006.01) | |
| A61K 8/97 | (2017.01) | |
| A61K 9/68 | (2006.01) | |
| A61P 1/02 | (2006.01) | |
| A61Q 11/00 | (2006.01) | |
| A61K 31/223 | (2006.01) | |
| A61K 36/575 | (2006.01) | |
| A61K 31/198 | (2006.01) | |

(52) U.S. Cl.
CPC ............ *A61K 36/575* (2013.01); *A23G 3/364* (2013.01); *A23G 3/44* (2013.01); *A23G 3/48* (2013.01); *A23G 4/068* (2013.01); *A23G 4/12* (2013.01); *A23G 4/14* (2013.01); *A61K 8/44* (2013.01); *A61K 8/97* (2013.01); *A61K 9/0058* (2013.01); *A61K 31/198* (2013.01); *A61K 31/223* (2013.01); *A61P 1/02* (2018.01); *A61Q 11/00* (2013.01); *A61K 2300/00* (2013.01)

(58) Field of Classification Search
CPC ............ A61K 8/64; A61K 8/988; A61K 8/98; A61Q 11/00
USPC ............................................... 424/48, 49, 58
See application file for complete search history.

(56) References Cited

U.S. PATENT DOCUMENTS

| 7,347,985 B2 * | 3/2008 | Maxwell ................ A23G 3/48 424/435 |
|---|---|---|
| 2006/0013779 A1 | 1/2006 | Dodds |
| 2006/0140885 A1 | 6/2006 | Gaffar |
| 2007/0140990 A1 | 6/2007 | Fetissova |
| 2007/0154863 A1 * | 7/2007 | Cai ................ A46B 11/0058 433/89 |
| 2012/0225942 A1 | 9/2012 | Stockel |
| 2013/0078197 A1 | 3/2013 | Mello |
| 2013/0266521 A1 * | 10/2013 | Fetissova ................ A61K 8/21 424/50 |
| 2015/0098934 A1 * | 4/2015 | Lee ................ A61K 8/97 424/115 |
| 2016/0004298 A1 * | 1/2016 | Mazed ................ G06F 3/011 345/633 |

FOREIGN PATENT DOCUMENTS

WO   WO2009099450 A1   8/2009

* cited by examiner

*Primary Examiner* — Walter E Webb

(57) ABSTRACT

The present disclosure relates generally to oral compositions and methods for inhibiting the formation of plaque biofilm by salivary bacteria, and more particularly, to oral compositions comprising a combination of magnolia bark extract (MBE) and L-arginine, N$^{\alpha}$-lauroyl ethyl ester (LAE). The oral compositions are useful for improving oral health, including inhibiting the formation of plaque biofilm by salivary bacteria and reducing plaque adherence to teeth.

26 Claims, 6 Drawing Sheets

SYNERGISTIC ANTIBACTERIAL EFFECTS OF MAGNOLIA BARK EXTRACT AND L-ARGININE, N-α-LAUROYL ETHYL ESTER ON PLAQUE BIOFILM

CROSS-REFERENCE TO RELATED APPLICATIONS

This application claims the benefit of U.S. Provisional Application No. 62/217,213, filed Sep. 11, 2015, which is herein incorporated by reference in its entirety.

BACKGROUND OF THE DISCLOSURE

The present disclosure relates generally to oral compositions and methods for inhibiting the formation of plaque biofilm by salivary bacteria, and more particularly, to oral compositions comprising a combination of magnolia bark extract (MBE) and L-arginine, N$^\alpha$-lauroyl ethyl ester (LAE). The oral compositions are useful for improving oral health, including inhibiting the formation of plaque biofilm and reducing plaque formation and adherence to teeth.

The oral cavity is comprised of more than 700 bacterial species (Aas, et al., "Defining the normal bacterial flora of the oral cavity," *J. Clin. Microbiol.*, 2005, Vol. 43(11), pp. 5721-32) that live together in symbiosis at times of good oral health (Zarco, et al., "The oral microbiome in health and disease and the potential impact on personalized dental medicine," *Oral. Dis.*, 2012, Vol. 18(2), pp. 109-20). An ecological shift in the oral microbiome, due to various extrinsic or intrinsic stimuli, can result in an abundance of certain pathogenic bacterial strains and cause oral disease, such as caries, gingivitis, and/or halitosis. The key to maintenance of oral health is maintaining the symbiotic nature of the oral microbiome and preventing overgrowth of pathogenic species within the oral biofilm. This is largely achieved by regular oral hygiene, such as tooth brushing, which mechanically removes the oral biofilm. Dental floss, toothpicks, mouth rinses, and chewing gum have also been promoted as adjuncts to regular oral hygiene (see Imfeld, T., "Chewing gum—facts and fiction: A review of gum-chewing and oral health," *Crit. Rev. Oral Biol. Med.*, 1999, Vol. 10(3), pp. 405-19; Crocombe, et al. "Is self interdental cleaning associated with dental plaque levels, dental calculus, gingivitis and periodontal disease?" *J. Periodontal Res.*, 2012, Vol. 47(1), pp. 188-97).

Dental plaque is a highly complex biofilm consisting of over 300 microbials, their metabolites, and salivary pellicles that form on the teeth within a short time after brushing. One of the challenges in preventing the formation of dental plaque lies in the nature of plaque biofilm. In particular, plaque biofilm has a complex structure that protects salivary bacteria from xenobiotics (Marsh, P. D. (2004). "Dental plaque as a microbial biofilm" *Caries Research*, 38(3):204-211). The complexity of the biofilm structure limits diffusion of antimicrobials into the biofilm matrix, resulting in protection of bacteria within the biofilm from exposure to the antimicrobial agent. In addition, it has been suggested that bacteria in plaque biofilm form symbiotic relationships to protect each other by metabolizing substances that threaten other microbials in the biofilm (Busscher H. J., Evans L. V., Editors. 1998. *"Oral Biofilms and Plaque Control,"* CRC Press. ISBN 978-90-5702-391-0). Thus, it is easier to prevent formation of plaque than to remove an established plaque. To either remove or penetrate an existing biofilm, it may be necessary to use surfactants, abrasives, enzymes or other agents that would aid in the penetration and removal of the plaque.

Two major mechanisms of action for plaque prevention are: 1) antimicrobial agents and 2) glucosyl transferase (GTF) inhibition. Antimicrobial agents that have been shown to have definite plaque-reducing abilities include chlorhexidine, cetylpyridinium chloride (CPC), triclosan and delmopinol. These are all medicinal and non-natural antimicrobial agents. Essential oils such as thymol, eucalyptol, methyl salicylate, and menthol along with other essential oils in an alcohol-based vehicle have also been found to reduce plaque. While thymol is most effective in reducing plaque, it has a disagreeable taste. Generally, these oils benefit from the presence of an alcohol to facilitate their solubility and penetration of the plaque biofilm. Furthermore, while suitable for oral treatments, such as mouthwashes, high concentrations of alcohols can leave a bitter aftertaste in oral compositions, such as gums, mints, edible films, confectioneries, and the like. While there are several GTF inhibitors reported in scientific publications and patents, their potential for use in oral compositions and confections has not been tested.

There is thus a need for other oral compositions that can be used to facilitate removal of bacteria from the oral cavity and inhibit the formation of plaque biofilm by salivary bacteria.

SUMMARY OF THE DISCLOSURE

The present disclosure relates generally to oral compositions and methods for oral cleansing and inhibiting the formation of plaque biofilm by salivary bacteria, and more particularly, to oral compositions comprising a combination of magnolia bark extract (MBE) and L-arginine, N$^\alpha$-lauroyl ethyl ester (LAE). The oral compositions are useful for improving oral health, including inhibiting the formation of plaque biofilm, and reducing plaque formation and adherence to teeth.

Thus, in one aspect, the present disclosure is directed to an oral composition for inhibiting the formation of plaque biofilm by salivary bacteria in an oral cavity of a consumer, the composition comprising MBE and LAE, wherein the oral composition comprises the MBE and LAE in amounts that provide a synergistic inhibition of the formation of plaque biofilm in the oral cavity. In various embodiments, the oral composition may comprise the MBE and LAE in a weight ratio of from about 16:1 to about 4:1.

In another aspect, the present disclosure is directed to a coated oral composition for inhibiting the formation of plaque biofilm by salivary bacteria in an oral cavity of a consumer, the coated oral composition comprising MBE and LAE in amounts that provide a synergistic inhibition of the formation of plaque biofilm in the oral cavity.

In another aspect, the present disclosure is directed to a method of making a coated oral composition, the method comprising: pretreating MBE and LAE to form a preblend mixture; adding the preblend mixture to a coating syrup; and, applying the coating syrup to an oral composition to produce the coated oral composition, wherein the coated oral composition comprises MBE and LAE in amounts that provide a synergistic inhibition of the formation of plaque biofilm by salivary bacteria in an oral cavity of a consumer. In various embodiments, the pretreating may comprise sieving the MBE and LAE, sonicating the MBE and LAE, and/or blending the MBE and LAE with one or more organoleptic components.

In another aspect, the present disclosure is directed to a method of making a chewing gum composition, the method comprising: pretreating MBE and LAE to form a preblend mixture; and forming the chewing gum composition from the preblend mixture, wherein the chewing gum composition comprises MBE and LAE in amounts that provide a synergistic inhibition of the formation of plaque biofilm by salivary bacteria in an oral cavity of a consumer. In various embodiments, the pretreating may comprise sieving the MBE and LAE, sonicating the MBE and LAE, and/or blending the MBE and LAE with a powdered gum base.

In another aspect, the present disclosure is directed to a method for inhibiting the formation of plaque biofilm in an oral cavity of a mammalian subject, the method comprising: contacting an oral composition of the present disclosure with the oral cavity of the subject.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A depicts the red fluorescence area of the labial surfaces of the anterior teeth (canine to canine, minimum (Mn), maximum (Mx)). FIG. 1B depicts the percentage of red fluorescence area against entire tooth surface.

FIG. 2 shows the average pH of dispersions of the plaque biomass obtained at time of plaque collection (0 hour), or after 2 or 4 hours of incubation.

DETAILED DESCRIPTION OF THE DISCLOSURE

Figure 1A:
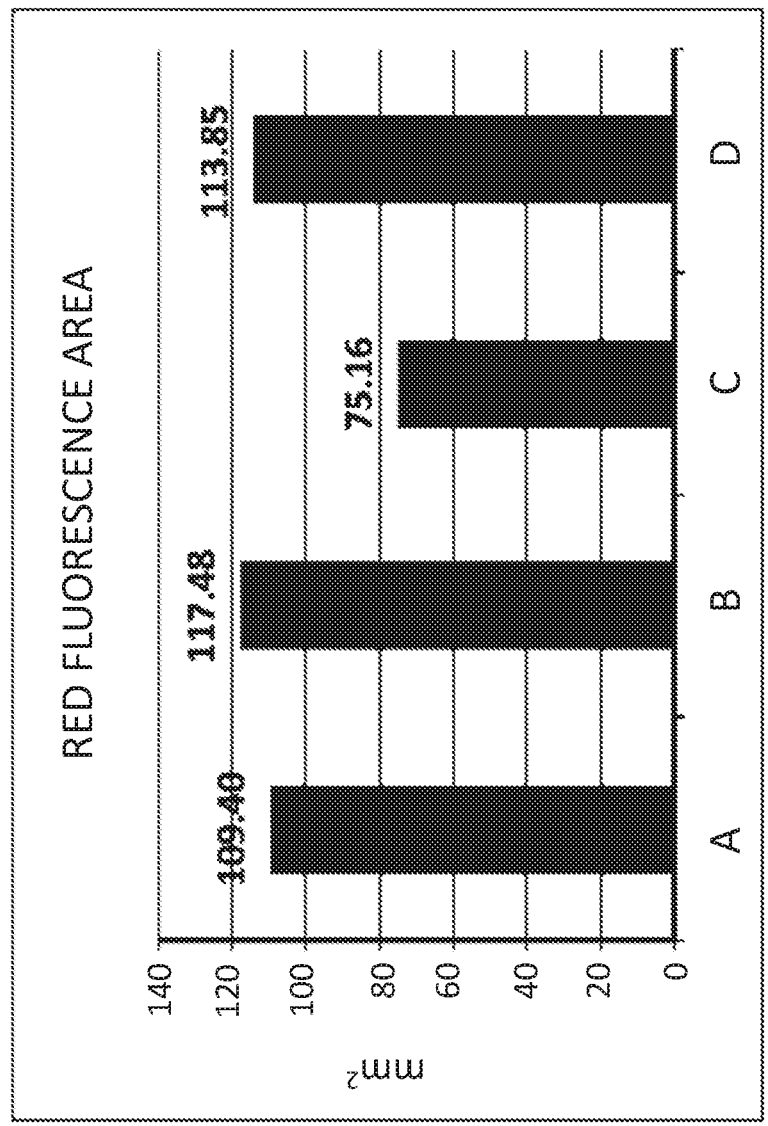
FIGS. 1A and 1B are graphs depicting the Qualitative Light Induced Fluorescence (QLF) Results, as discussed in Example 2.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The present disclosure relates generally to oral compositions and methods for oral cleansing and inhibiting the formation of plaque biofilm by salivary bacteria. More particularly, the present disclosure relates to oral compositions comprising a combination of magnolia bark extract (MBE) and L-arginine, $N^{\alpha}$-lauroyl ethyl ester (LAE). The oral compositions are useful for improving oral health, including inhibiting the formation of plaque biofilms in the oral cavity, and in particular, on teeth, and for reducing plaque adherence to teeth.

In particular, plaque (also referred to as "dental plaque" or "plaque biofilm") is a biofilm or mass of bacteria that grows on surfaces within the oral cavity. Plaque may lead to various oral diseases such as caries and periodontal diseases. *Streptococcus mutans* (a Gram-positive, faculatively anaerobic bacteria) is one of the primary components of plaque and causes of dental caries.

Surprisingly, it has now been discovered that MBE in combination with LAE is synergistically effective at inhibiting the formation of plaque biofilm by salivary bacteria. As used herein, "synergy" or "synergistic effect" refers to the effect that occurs when chemical substances or biological structures interact, and result in an overall effect that is greater than the sum of individual effects of any of them. Incorporating the combination of an effective amount of MBE and LAE into an oral composition can thus provide an oral composition that inhibits the formation of plaque biofilm by salivary bacteria. The oral compositions of the present disclosure may also be effective for use in the removal of existing plaque.

As used herein, the term "efficacious" means producing or capable of producing a desired effect. Moreover, "effective amount" or "effective concentration" refers to the level, amount, serving, or percent which produces or is capable of producing a desired effect. All percentages and ratios used herein are by weight of the total composition and all measurements made are at 25° C., unless otherwise designated Thus, in another aspect, the present disclosure is directed to a method for inhibiting the formation of plaque biofilm by salivary bacteria in an oral cavity of a mammalian subject. The method comprises contacting a composition of the present disclosure with the oral cavity of said subject. The mammalian subject may be human or a non-human animal In still another embodiment, the present disclosure is directed to a method of making a coated oral composition. The method comprises pretreating MBE and LAE to form a preblend mixture, adding the preblend mixture to a coating syrup, and applying the coating syrup to an oral composition to produce the coated oral composition. The MBE and LAE may be pretreated by sieving the MBE and LAE prior to addition to the coating syrup; sonicating the MBE and LAE prior to addition to the coating syrup; blending the MBE and LAE with one or more organoleptic components prior to addition to the coating syrup; or combinations thereof.

In still other embodiments, the present disclosure is directed to a method of making a chewing gum composition. The method comprises pretreating MBE and LAE to form a preblend mixture, and forming the chewing gum composition from the preblend mixture. The MBE and LAE may be pretreated by sieving the MBE and LAE; sonicating the MBE and LAE; blending the MBE and LAE with a powdered gum base; or combinations thereof.

Without wishing to be bound to any particular theory, it is believed that pretreating the MBE and LAE results in an improved loading efficiency and release rate of the MBE from the oral composition, as compared to oral compositions comprising MBE alone, or compositions comprising MBE and LAE that are not pretreated. In particular, in certain embodiments, pretreating by sieving the actives and sonicating to dissolve the actives results in a loading efficiency of greater than 90% in conventional chewing gums. Pretreating thus improves loading efficiency in chewing gum from about 50% to about 90%.

Magnolia Bark Extract

The compositions of the present disclosure comprise extract of magnolia (also referred to herein as "magnolia extract," "magnolia bark extract," or "MBE"). As referred to herein, such an "extract" of magnolia is an extract from dried cortex, or bark, of a plant from the Magnoliaceae family, such as *Magnolia officinalis*, ("magnolia") or a synthetic or semi-synthetic equivalent of such an extract or an active component or compound thereof. Typically, extracts of Magnolia Cortex (the bark of *Magnolia officinalis*) contain hydrophobic compounds including magnolol, honokiol, tetrahydromagnolol, and tetrahydrohonokiol. Any plant from the Magnoliaceae family is suitable for the present invention and may be used in alternate embodiments, preferably such that the extract comprises an effective concentration of a compound selected from the group consisting of magnolol, honokiol, tetrahydromagnolol, tetrahydrohonokiol, and combinations thereof, and preferably an effective concentration of magnolol and/or honokiol. Preferably, an effective concentration of magnolia extract (or an active(s) therein) is a concentration that results in a reduction in the formation of plaque biofilm or in the presence of an existing plaque biofilm when used in combination with LAE. Preferably, the effective concentration of magnolia extract is such that a synergistic inhibition in the formation of plaque biofilm by salivary bacteria is achieved when the magnolia extract is used in combination with LAE.

As used herein, "extracting" or "extraction" of a solid or liquid material means contacting the material with an appropriate solvent to remove the substance(s) desired to be extracted from the material. Where the material is solid, it is preferably dried and crushed or ground prior to contacting it with the solvent. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

In one embodiment, magnolia extract is made from dried Magnolia plant bark and can be prepared by extracting the bark using an appropriate solvent. Solvents include compatible liquids such as hydrocarbons and substituted hydrocarbons.

In preferred embodiments, the natural extract active ingredients used in oral compositions are reproducible, stable, and have microbiological safety. In one embodiment of the present invention, the magnolia extract is isolated by supercritical fluid extraction (SFE) using carbon dioxide ($CO_2$). Supercritical fluids use a solvent that is readily available, inexpensive, and environmentally safe (such as $CO_2$). Carbon dioxide is non-toxic, non-explosive, readily available and easily removed from the extracted products. In certain embodiments, SFE extraction produces a much lighter color of magnolia extract (a light beige product) that is particularly suitable for aesthetically pleasing oral composition formulations.

In various embodiments, it is preferred that the active ingredient in the magnolia extract comprises either magnolol, honokiol, or both. Magnolol and honokiol are non-ionic hydroxybiphenyl compounds, the structures of which are believed to be as follows:

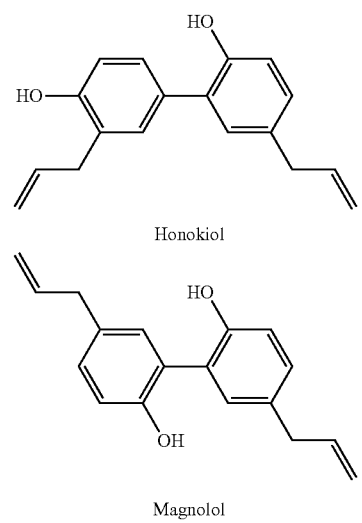

Honokiol

Magnolol

Additionally, tetrahydromagnolol and tetrahydrohonokiol are hydrogenated analogs of magnolol and honokiol often found in relatively small concentrations in the extracts of magnolia, and as such may be included in the composition.

Thus, as will be described in greater detail below, in various embodiments of the present invention, the magnolia extract comprises one or more hydrophobic compounds: magnolol, honokiol, tertrahydromagnolol, tetrahydrohonokiol, and mixtures thereof, which are used in combination with LAE to inhibit the formation of plaque biofilm by salivary bacteria in the oral cavity.

In various embodiments, magnolia extract of the present invention comprises magnolol, honokiol, or both in an amount of about 2% to about 99% by weight. In other embodiments, magnolia extract comprises magnolol, honokiol, or both in an amount greater than 50% by weight. In one embodiment of the present invention, the magnolol is present in an amount greater than 50% by weight, preferably greater than 70% by weight, or most preferably, greater than 90% by weight. In another embodiment, honokiol is present in an amount less than 50% by weight, more preferably in an amount less than 30% by weight, or, most preferably, less than 10% by weight.

The MBE may be present in the oral composition in an amount of from 0.001 to about 10% by weight. In some embodiments, the MBE is present in the oral composition in an amount of about 0.001 to about 5.0% by weight, or about 0.001 to about 2.0% by weight. In another embodiment, the MBE is present in the oral composition in an amount of about 1.0 to about 2.0% by weight. In other embodiments, the MBE is present in amounts less than 1% by weight, for example the MBE may be present in the oral composition in an amount of from about 0.01 to about 1% by weight. In a preferred embodiment, the MBE is present in an amount from about 0.01 to 0.5% by weight. Most preferably, the MBE is present in the oral compositions in an amount sufficient to provide a synergistic weight ratio of the MBE to the LAE in the composition. In particular, the MBE is preferably present in the oral compositions in combination with LAE in an amount sufficient to inhibit the formation of plaque biofilm by salivary bacteria.

In various embodiments, the oral compositions will comprise from about 1 to about 20 mg of MBE. In another aspect, the oral compositions will comprise from about 1 to about 10 mg of MBE.

L-Arginine, N$^\alpha$-Lauroyl Ethyl Ester

In addition to the MBE, the oral compositions of the disclosure further comprise L-Arginine, N$^\alpha$-Lauroyl Ethyl Ester (LAE). LAE is also known as lauric arginate ethyl ester, lauramide arginine ethyl ester, N-lauroyl-L-arginine ethyl ester, ethyl-N$^\alpha$-lauroyl-L-arginate.HCl, and INS No. 243. It is a cationic amino acid derivative that may be used as a food preservative. LAE has bacteriostatic activity against Gram positive bacteria, Gram negative bacteria, molds, yeasts, and other food spoilage microorganisms (see Rodriguez, E., et. al, "Cellular effects of monohydrochloride of L-arginine, N$^\alpha$-lauroyl-ethyl ester (LAE) on exposure to *Salmonella typhimurium* and *Staphylococcus aureus*", *J. Applied Microbio.*, 2004, Vol. 96(5), 903-912). LAE is a derivative of lauric acid, L-arginine, and ethanol, and metabolism of LAE yields L-arginine, ethanol, and lauric acid, which are three common components of a normal diet (see Ruckman, S., et. al, "Toxicological and metabolic investigations of the safety of N$^\alpha$-lauroyl ethyl ester monohydrochloride (LAE)", *Food and Chemical Toxicology*, 2004, Vol. 42, 245-259).

The neutral, non-salt form of LAE is shown below:

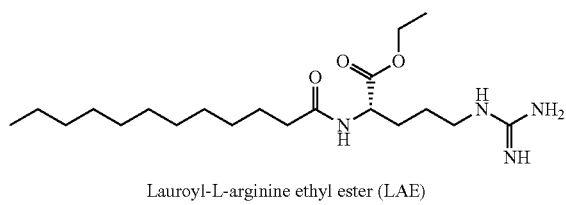 [SMILES: CCCCCCCCCCCC(=O)N[C@@H](CCCNC(=N)N)C(=O)OCC]

Lauroyl-L-arginine ethyl ester (LAE)

LAE may form both neutral and cationic salts. As used herein, "LAE" is intended to cover both the salt and neutral forms, unless otherwise indicated.

In some embodiments, the LAE is food grade and is suitable for use as a food additive. It has been designated by the United States FDA as generally regarded as safe (GRAS) or FEMA GRAS (Intl. Flavor Manuf. Assoc.). In one non-limiting example, LAE is the cationic monohydrochloride salt. LAE is commercially available, and is sold under the trade name MIRENAT®-P/100 by Vedeqsa of Barcelona, Spain.

The LAE is present in the oral composition in an amount of from 0.001 to about 10% by weight. In some embodiments, the LAE is present in the oral composition in an amount of about 0.001 to about 5.0% by weight, or about 0.001 to about 2.0% by weight. In another embodiment, the LAE is present in the oral composition in an amount of about 1.0 to about 2.0% by weight. In other embodiments, the LAE is present in amounts less than 1% by weight, for example the LAE may be present in the oral composition in an amount of from about 0.01 to about 1% by weight. In a preferred embodiment, the LAE is present in an amount from about 0.01 to 0.5% by weight. Most preferably, the LAE is present in the oral compositions in an amount sufficient to provide a synergistic weight ratio of the MBE to the LAE in the composition. In particular, the LAE is preferably present in the oral compositions in combination with MBE in an amount sufficient to result in a synergist inhibition of the formation of plaque biofilm by salivary bacteria.

In various embodiments, the oral compositions will comprise from about 1 to about 20 mg of LAE. In another aspect, the oral compositions will comprise from about 1 to about 10 mg of LAE.

Oral Composition

The oral compositions of the present disclosure comprising MBE and LAE are in the form of a food-acceptable or food contact acceptable material or carrier in which the MBE and LAE may be incorporated or dispersed without adverse effect. The oral composition may be a water-soluble solid or chewable solid such as chewing gums (e.g., tablet gums, pellet gums, stick gums, compressed gums, co-extruded layered gums, bubble gums, etc.), confections (e.g., mints, hard candies, chewy candies, chocolates, gels, confectionery pastes, etc.), or orally soluble tablets, beads, or lozenges. In some embodiments, the composition is a confectionery composition in the form of a coating, shell, film, syrup, or suspension. Such delivery systems are well known to one of skill in the art, and preparation generally entails stirring the MBE and LAE into a warm base with flavor, non-cariogenic sweeteners and additional organoleptic components. In some embodiments, the oral composition may be suitable for use by non-human mammals, and may be, for example, an animal treat biscuit.

As discussed herein, the oral compositions of the present disclosure preferably comprise a synergistic weight ratio of MBE to LAE. In certain embodiments, the weight ratio of MBE to LAE is preferably such that the oral composition provides a synergist inhibition of the formation of plaque biofilm by salivary bacteria in the oral cavity of a consumer of the oral composition. In such embodiments, the MBE and LAE are typically present in the oral composition in a weight ratio of from about 16:1 to about 4:1, including from about 16:1 to about 8:1, or from about 8:1 to about 4:1.

In certain embodiments, the synergistic inhibition of plaque biofilm by salivary bacteria in the oral cavity may occur after chewing the oral composition for at least 10 minutes, including for at least 20 minutes.

One method of evaluating the efficacy of LAE and MBE against salivary bacteria is by determining the minimum inhibitory concentration (MIC). One suitable method for determining MIC is described in U.S. Pat. No. 7,470,442, which is herein incorporated by reference. Briefly, chlorhexidine is used as a positive control and sterile water is used as a negative control. Methanol and Tween 80 are used as a solvent for MBE. Tween 80 is the common name for Polysorbate 80. Ninety-six-well microtiter plates are used for this study. Each well contained $5 \times 10^5$ CFU/ml of bacteria, serially diluted agents and bacterial growth medium. All bacterial cultures are incubated at 37° C. and stationary. Bacterial growth is estimated spectrophotometrically at 660 nm, after 48 hours. The MIC for each test bacteria was defined as the minimum concentration of test compound limiting turbidity to less than 0.05 absorbance at 660 nm.

Another method for evaluating the efficacy of LAE and MBE against salivary bacteria is by determining the minimum bactericidal concentration (MBC). One suitable method for determining MBC is described in U.S. Pat. No. 7,470,442. Briefly, the MBC is determined using the 96-well microtiter plate serial dilutions as described above for the MIC test. Serial dilutions of cultures in wells showing no visible growth are performed and 10 microliters of culture are plated in triplicate on blood agar plates. Viable colonies are scored after incubation of the plates for 48 hours at 37° C. For each test bacterium, the number of CFU/ml is determined in the initial inoculum. The MBC is defined as the lowest concentration of a test compound that killed at least 99.9% of the cells present in the initial inoculum.

Chewing Gums

In one embodiment, the oral composition of the present disclosure is a chewing gum. The chewing gum may include the MBE and LAE in any of the amounts or weight ratios set forth herein. In certain embodiments, the chewing gum comprises MBE and LAE in amounts such that the chewing gum provides a synergistic inhibition of the formation of plaque biofilm by salivary bacteria. In such embodiments, MBE and LAE are preferably present in the gum in a weight ratio of from about 16:1 to about 4:1.

Chewing gum products of the present disclosure may be made using a variety of different compositions that are typically used in chewing gum compositions. Suitable physical forms include sticks, tabs, chunks, solid balls, hollow balls, pellets, layers, and the like. Although exact ingredients for each product form will vary from product to product, the specific techniques will be known by one skilled in the art. In general, a chewing gum composition typically contains a water-insoluble chewable gum base portion, and a water-soluble bulk portion which includes water soluble bulking agents (i.e., sugars, polyols) and other water soluble components and perhaps other active ingredients which are typically water-insoluble. The water-soluble portion dissipates with a portion of the flavor over a period of time during chewing. The gum base portion is retained in the mouth throughout the chew.

The chewing gum may comprise between approximately 5% to about 95% by weight gum base. Typically, the insoluble gum base may comprise between approximately 10% and about 50% by weight of the gum, or from approximately 20% to about 40% by weight of the gum. The present disclosure contemplates employing any commercially acceptable gum base.

In general, the insoluble gum base may comprise elastomers, elastomer solvents, plasticizers, waxes, emulsifiers, and inorganic fillers. Plastic polymers, such as polyvinyl acetate, which behave somewhat as plasticizers, are also included. Other plastic polymers that may be used include polyvinyl laurate, polyvinyl alcohol, and polyvinyl pyrrolidone. Gum base may comprise as low as 5% or as high as 95% by weight, or more typically 20 to 40% by weight of the overall chewing gum composition.

Elastomers provide the rubbery texture which is characteristic of chewing gum. Elastomers typically make up about 5 to about 25% by weight of the gum base. Synthetic elastomers may include, but are not limited to, polyisobutylene, butyl rubber (isobutylene-isoprene copolymer), styrene copolymers (having for example a styrene-butadiene ratio of about 1:3 to about 3:1), polyisoprene, polyethylene, vinyl acetate-vinyl laurate copolymer, and combinations thereof.

Natural elastomers may include for example natural rubbers such as smoke or liquid latex and guayule, as well as natural gums such as chicle, jelutong, lechi caspi, perillo, sorva, massaranduba balata, massaranduba chocolate, nispero, rosindinha, gutta hang kang and mixtures thereof. Preferred elastomers will depend on, for example, whether the chewing gum in which the base is used is adhesive or conventional, synthetic or natural, bubble gum or regular gum. Elastomers provide the rubbery texture which is characteristic of chewing gum.

Elastomer solvents which are sometimes referred to as elastomer plasticizers, include but are not limited to natural rosin esters such as glycerol esters, or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerthyritol esters of rosin, synthetics such as terpene resins, polylimonene and other polyterpenes and/or any suitable combination of the forgoing. Elastomer solvents are typically employed at levels of 5 to 30% by weight of the gum base.

Gum base plasticizers are sometimes referred to as softeners. Typically, these include fats and oils as well as waxes. Fats and oils are typically vegetable oils which are usually partially or fully hydrogenated to increase their melting point. Vegetable oils suitable for such use include oils of cottonseed, soybean, palm (including palm kernal), coconut, shea, castor, peanut, corn, rapeseed, canola, sunflower, cocoa and others. Animal fats such as milk fat, tallow and lard may also be used. Commonly employed waxes include paraffin, microcrystalline and natural waxes such as beeswax and carnauba. Plasticizers are typically employed at a level of 5 to 40% by weight of the gum base.

Gum bases commonly contain optional additives such as antioxidants and colors which serve their normal functions. Less commonly, flavors and sweeteners may be added to the gum base. These additives, if used, are typically employed at levels of about 1% or less by weight of the gum base.

The chewing gum and/or gum base may also include a filler component. The filler component is typically an inorganic powder such as calcium carbonate, ground limestone, magnesium carbonate, talc, silicate types such as aluminum and magnesium silicate, dicalcium phosphate, tricalcium phosphate, cellulose polymers, such as wood, combinations thereof and the like. The filler may constitute from 5% to about 50% by weight of the chewing gum.

Commonly used emulsifiers include mono- and diglycerides, such as glycerol monostearate, lecithin, glycerol triacetate, glycerol monostearate, acetylated monoglycerides, fatty acids, and combinations thereof. Emulsifiers are commonly used at a level of 1 to 10% by weight of the chewing gum.

The water-soluble portion of the chewing gum may comprise softeners, sweeteners, flavoring agents, and combinations thereof as well as other optional ingredients. For example, the majority of the water soluble portion of the chewing gum will typically comprise a water-soluble, powdered carbohydrate which serves as a bulking agent. In sugar gums, this most often is sucrose although other sugars such as fructose, erythrose, dextrose (glucose), levulose, tagatose, galactose, trehalose, corn syrup solids and the like, alone or in any combination may also be used.

Generally, sugarless chewing gums will employ sugar alcohols (also called alditols, polyols or polyhydric alcohols) as bulking agents due to their benefits of low cariogenicity, reduced caloric content and reduced glycemic values. Such sugar alcohols include sorbitol, mannitol, xylitol, hydrogenated isomaltulose, maltitol, erythritol, hydrogenated starch hydrolysate solids, and the like, alone or in any combination. Longer chain saccharides such as polydextrose and fructo-oligosaccharides are sometimes employed for their reduced caloric properties and other health benefits. The bulking agents typically comprise approximately 5% to about 95% by weight of the gum composition.

Softeners, also known in the art as plasticizers or plasticizing agents, generally constitute between approximately 0.5% to about 15% by weight of the chewing gum. These include glycerin, propylene glycol and aqueous sweetener solutions (syrups). Examples of syrups include corn and glucose syrups which are usually prepared from hydrolyzed starch. For sugarless products, the starch hydrolysate may be hydrogenated to produce an ingredient known as hydrogenated starch hydrolysate syrups or maltitol syrups.

In the case of sugarless gums, it is usually desirable to add high potency sweeteners to compensate for the reduced sweetness resulting from substitution of sugar alcohols for the sucrose in sugar gums. High potency sweeteners may be defined as food acceptable compounds which are at least twenty times sweeter than sucrose. Commonly used high potency sweeteners include, but are not limited to, aspartame, sucralose, acesulfame-K, saccharin, thaumatin, alitame, neotame, and cyclamate, as well as natural or plant-sourced sweeteners, such as perilla, stevia, monatin, monellin and chalcones.

Usage levels for high potency sweeteners may vary widely depending on the potency of the sweetener, local market preferences, taste, and the regulatory environment. Typical levels can range from about 0.01% to about 5% by weight, although some applications may dictate usage outside that range. These sweeteners may be combined together, or with non-high potency sweeteners at varying levels to impart a desired sweetness to the overall composition.

Flavors can be employed to impart a characteristic aroma and taste sensation to chewing gum products. These flavors may be natural or artificial (synthetic) in origin, or a combination of both. Although the range and combinations of flavors usable in chewing gums is nearly limitless, they commonly include fruit flavors, such as lemon, orange, lime, grapefruit, tangerine, strawberry, apple, cherry, raspberry, blackberry, blueberry, banana, pineapple, cantaloupe, muskmelon, watermelon, grape, currant, mango, kiwi and many others as well as combinations. Mint flavors include spearmint, peppermint, wintergreen, basil, corn mint, menthol and others and mixtures thereof. Spice flavors include cinnamon, vanilla, clove, chocolate, nutmeg, coffee, licorice, eucalyptus, ginger, cardamom and many others. Also used are herbal and savory flavors such as popcorn, chili, corn chip and the like. Flavors are typically employed at levels of 0.1 to 10% by weight of the finished gum product.

The chewing gum (along with any of the oral compositions) of the present disclosure may employ various sensates or organoleptic components. Generally, sensates may be any compounds that cause a cooling, heating, warming, salivating, tingling or numbing, for example, to the mouth or skin.

The organoleptic components are optionally selected from the group consisting of a flavoring agent, a cooling agent, a heating agent, a mouthfeel agent, a tingling agent, a sweetening agent, a souring agent, a salivating agent, a bittering agent, a teeth whitening agent, an anti-cavity agent, a breath freshening agent, an audible agent, and combinations thereof. These are well known in the art and are selected based on the desired profile of the gum or oral composition.

Cooling agents encompass any number of physiological cooling agents but do not include traditional flavor-derivatives such as menthol or menthone. Preferred cooling agents provide a cooling effect without imparting perceptible flavor of their own. Cooling agents are perceived as cold or cool when contacted with the human body and, in particular, with the mucous membranes of the mouth, nose and throat. Cooling agents may be natural or synthetic chemicals used to impart a cooling sensation with minimal aroma. Commonly employed cooling agents include ethyl p-menthane carboxamide and other N-substituted p-menthane carboxamides, N,2,3-trimethyl-2-isopropyl-butanamide and other acyclic carboxamides, menthyl glutarate, 3-1-menthoxypropane-1,2-diol, isopulegol, menthyl succinate, menthol propylene glycol carbonate, ethylene glycol carbonate, menthyl lactate, menthyl glutarate, p-menthane-1,8-diol, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and others and combinations thereof.

Trigeminal stimulants other than cooling agents may be employed in the chewing gums of the present disclosure. These include warming agents such as capsaicin, capsicum oleoresin, red pepper oleoresin, black pepper oleoresin, piperine, ginger oleoresin, gingerol, shoagol, cinnamon oleoresin, cassia oleoresin, cinnamic aldehyde, eugenol, cyclic acetal of vanillin, menthol glycerin ether and unsaturated amides and tingling agents such as Jambu extract, vanillyl alkyl ethers such as vanillyl n-butyl ether, spilanthol, *Echinacea* extract and Northern Prickly Ash extract.

Chewing gum generally conveys oral care benefits. In addition to mechanical cleaning of the teeth provided by the chewing action, saliva stimulated by chewing, flavor and taste from the product conveys additional beneficial properties in reducing bad breath, neutralizing acid, and the like.

The chewing gums of the present disclosure can provide these benefits along with the benefits disclosed herein, and may also be used as vehicles for the delivery of specialized oral care agents. For example, breath freshening agents include salts of zinc, salts of copper, polyphenols, mushroom extracts and mixtures thereof. Mouth odor masking flavors such as cinnamon, mint, wintergreen, fruit flavors and mixtures thereof may also be used. Other dental actives, for example, tooth whiteners, fluoride, stain removers, calcium salts, phosphate salts and mixtures thereof, can also be used.

The chewing gums of the present disclosure may be used to deliver biologically active agents to the chewer. Biologically active agents include vitamins, minerals, anti-oxidants, nutritional supplements, dietary supplements, functional food ingredients (e.g., probiotics, prebiotics, lycopene, phytosterols, stanol/sterol esters, omega-3 fatty acids, adenosine, lutein, zeaxanthin, grape seed extract, ginkgo biloba, and the like), OTC and prescription pharmaceuticals, vaccines, and nutritional supplements.

It may be desirable to take certain steps to increase or decrease the rate of the release of the agents or other ingredients (e.g., sweeteners, flavors) or to ensure that at least a minimum quantity is released. Such measures as encapsulation, isolation of the active, and measures to increase or decrease interactions of actives and ingredients may be employed to that end. These techniques are well known to one skilled in the art.

In general by way of a non-limiting example, chewing gum is manufactured by simultaneously or sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

The LAE and MBE may be incorporated simultaneously or sequentially into the center portion of the gum and/or a gum coating. For instance, in certain embodiments, the LAE and MBE are combined and then incorporated into a center layer of the gum, or are center filled, using any suitable technique known in the art. In certain embodiments, the LAE and MBE are combined and then incorporated in the coating of a gum using any suitable technique known in the art, such as described herein.

In another embodiment, the LAE is incorporated into the center portion of the gum, and the MBE is incorporated into the gum coating. For instance, in certain embodiments, the LAE is incorporated into a center layer of the gum, or is center filled, using any suitable technique known in the art, while the MBE is incorporated into a coating syrup or coating flavor, such as described hereinafter.

In another embodiment, the MBE is incorporated into the center portion of the gum, and the LAE is incorporated into the gum coating. For instance, in certain embodiments, the MBE is incorporated into a center layer of the gum, or is center filled, using any suitable technique known in the art, while the LAE is incorporated into a coating syrup or coating flavor, such as described hereinafter.

Chewing gums of the present invention may also be coated. Pellet or ball gum is prepared as conventional chewing gum, but formed into pellets that are pillow shaped, or into balls. The pellets/balls can be then coated or panned by conventional panning techniques to make a unique coated pellet gum.

Conventional panning procedures generally coat with sugars and other polyols, including, but not limited to, sucrose, dextrose, maltose, palatinose, xylitol, lactitol, maltitol, hydrogenated isomaltulose and other alditols or a combination thereof.

These materials may be blended with panning modifiers including, but not limited to, gum arabic, maltodextrins, corn syrup, gelatin, cellulose type materials like carboxymethyl cellulose or hydroxymethyl cellulose, starch and modified starches, insoluble carbonates like calcium carbonate or magnesium carbonate and talc. Antitack agents may also be added as panning modifiers which allow the use of a variety of carbohydrates and sugar alcohols to be used in the development of new panned or coated gum products. Flavors, sweeteners, and other organoleptic components may also be added with the coating with MBE and/or LAE to yield unique product characteristics.

The MBE and the LAE can be easily added to the coating syrup/solution prepared for panning. In another embodiment, MBE and LAE can be used as a powder alone or blended with other components and used in conventional panning procedures. In some embodiments, the MBE and LAE each independently comprise from 0.001% to 5% by weight of the coating. In some embodiments, the MBE and LAE are each independently of the other present in the coating in an amount of about 0.001 to about 5.0% by weight, or about 0.001 to about 2.0% by weight. In another embodiment, the MBE and LAE are present in the coating in an amount of about 1.0 to about 2.0% by weight. In other preferred embodiments, the MBE and LAE are present in the coating in amounts less than 1% by weight, for example they may be present in the coating in an amount of from about 0.01 to about 1% by weight.

In some aspects of the present disclosure, the MBE and LAE are present in the coating of the oral composition in an amount such that the oral composition provides a synergist inhibition of the formation of plaque biofilm by salivary bacteria in the oral cavity of a consumer of the oral composition. In such embodiments, MBE and LAE are preferably present in the coating of the oral composition in a weight ratio of from about 16:1 to about 4:1, including from about 16:1 to about 8:1, and from about 8:1 to about 4:1.

Candies/Confectionaries

As previously discussed, the oral compositions of the present disclosure may alternatively be in the form of a confectionery product, including for example mints, hard candies, chewy candies, coated chewy candies, tableted candies, chocolates, nougats, confectionery pastes and the like. These candies or confectionery products may comprise any of the various sugars and sweeteners, flavoring agents and/or colorants, as well as other components, known in the art and/or set forth above in the discussion of chewing gums. Additionally, these candies or confectionery products may be prepared using processing conditions and techniques known in the art. The candies or confectionery products may include the MBE and LAE in any of the amounts set forth herein. In one particular embodiment, the candies or confectionery products may comprise up to about 1.0% by weight of MBE and about 2.0% by weight of LAE.

Preferably, the candy or confectionery product comprises MBE and LAE in amounts such that the candy or confectionery product provides a synergistic inhibition of the formation of plaque biofilm by salivary bacteria in the oral cavity of a consumer of the oral composition. In such embodiments, MBE and LAE are preferably present in the candy or confectionery product in a weight ratio of from about 16:1 to about 4:1, including from about 16:1 to about 8:1, or from about 8:1 to about 4:1.

By way of a non-limiting example, a hard candy can be primarily comprised of corn syrup and sugar, and derives its name from the fact that it contains only between 1.0% and 4% by weight moisture. In appearance, these types of candies are solid, but they are actually supercooled liquids, which are far below their melting points. There are different types of hard candies. Glass types are usually clear or made opaque with dyes; and grained types, which are always opaque, due to entrapped air and/or moisture.

For illustrative purposes, it is to be noted that a continuous making process for making deposited glass types, with a sugar base can be generally made as follows. Sugar corn syrup mixture is spread over a cylinder heated by high pressure steam. Rapid head exchange causes the water in the syrup to evaporate. The cooked syrup is discharged, colors and flavors are added. These can be conveyed directly to hoppers which then discharge directly into molds. The candy is conveyed to batch rollers, which shapes and sizes the batch. The candy enters a former, which shapes the individual pieces into discs, balls, barrels, etc. The present disclosure can be made into any shape, circles, squares, triangles etc., also into animal shapes or any other novelty molding available. The candy is then cooled, wrapped and packaged.

For grained types of candy, water and sugar are the basic components being mixed with other ingredients, and cooked at high temperatures (290° F. to 310° F.), causing the water to turn to steam. The product is transferred to a cooling wheel, where it is collected in about 150 pound batches, placed in a pulling machine to aerate the product, and the flavor is added. The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at 90° F. and 60% humidity. The entrapped air and moisture causes the product to grain.

The MBE and LAE may be added at any suitable point during the manufacturing process, and typically during addition of the flavors.

Lozenges, Beads, and Tablets

In some embodiments, the oral composition may be a lozenge, bead, or tablet. The lozenge, bead, or tablet may include the MBE and LAE in any of the amounts set forth herein. In one embodiment, the lozenge, bead, or tablet may comprise up to about 1.0% by weight of MBE and about 2.0% by weight of LAE.

In one particular embodiment, the lozenge, bead, or tablet will comprise MBE and LAE in amounts such that the lozenge, bead, or tablet provides a synergistic inhibition of the formation of plaque biofilm by salivary bacteria in the oral cavity of a consumer. In such embodiments, the MBE and LAE are preferably present in a weight ratio of from about 16:1 to about 4:1.

The orally acceptable vehicle or carrier used to form a lozenge, bead, or tablet is typically a non-cariogenic, solid water-soluble polyhydric alcohol (polyol) such as, but not limited to, mannitol, xylitol, sorbitol, maltitol, erythritol, hydrogenated starch hydrozylate (HSH), hydrogenated glucose, hydrogenated disaccharides or hydrogenated polysaccharides, in an amount of about 85 to about 95% by weight of the total composition. Emulsifiers such as glycerin, and tableting lubricants, in minor amounts of about 0.1 to 5% by weight, may be incorporated into the tablet, bead or lozenge formulation to facilitate the preparation of the tablet beads and lozenges. Suitable lubricants include vegetable oils such as, but not limited to, coconut oil, magnesium stearate, aluminum stearate, talc, starch and polyethylene glycols. Suitable noncariogenic gums include kappa carrageenan, carboxymethyl cellulose, hydroxyethyl cellulose and the like.

A lozenge, bead, or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead, and lozenge, compositions of this embodiment affords a relatively longer time period of contact in the oral cavity with the MBE and LAE of the present invention.

In some embodiments, the oral composition is a lozenge. The lozenge may comprise a core in the form of a liquid, powder, syrup, suspension, fondant, toffee, or chocolate comprising the LAE, and a coating, such as described herein, comprising the MBE. In another embodiment, the lozenge may comprise a core comprising the MBE, and a coating, such as described herein, comprising the LAE.

In another embodiment, the MBE and LAE are both incorporated into the coating of the lozenge. Suitable amounts of MBE and LAE for inclusion in the coating include those set forth above for chewing gum coatings. In still another embodiment, the MBE and LAE are both incorporated into the core of the lozenge. Method for preparing these embodiments are well known in the art.

Animal Products

In some embodiments, the oral composition may be suitable for use by non-human mammals, and may be, for example, an animal treat (e.g., a biscuit).

Food products and supplements for animals are well known in the art and are preferably made with any suitable dough. Food supplement dough generally comprises at least one of flour, meal, fat, water, and optionally particulate proteinaceous particles (for texturization) and flavor. For instance, when the desired product is a biscuit, conventional dough can be used, optionally containing discrete particles of meat and/or meat by-products or farinaceous material. Examples of suitable dough for the production of hard and soft (including humectant for water control) animal biscuits are disclosed in U.S. Pat. Nos. 5,405,836; 5,000,943; 4,454,163; 4,454,164, the contents of each of which are incorporated herein by reference. Such compositions are preferably baked. The MBE and LAE may be added with the flavor, included in an interior reservoir with a soft center, or coated onto the surface of a baked food supplement by dipping or spraying. Preferably, the animal product will comprise MBE and LAE in amounts such that the animal product provides a synergistic inhibition of the formation of plaque biofilm by salivary bacteria. In one embodiment, the MBE and LAE are present in a weight ratio of from about 16:1 to about 4:1, including from about 16:1 to about 8:1, or from about 8:1 to about 4:1. Any other suitable means known to one of skill in the art for delivering active ingredients to animals may also be used.

Method of Preparation

In addition to the above-noted advantages to oral compositions comprising MBE and LAE, it has also surprisingly been discovered that inclusion of LAE in an oral composition in combination with MBE improves the loading efficiency of MBE and release rate of the MBE from the oral composition, as compared to oral compositions comprising MBE alone. This effect is further enhanced when the MBE and LAE are pretreated prior to incorporating them into the oral composition. In particular, it is believed that the loading efficiency and release rate of MBE from chewing gum can be increased by at least 20%, and typically by at least 33% when MBE and LAE are pretreated prior to incorporation into the oral composition. In particular, in certain embodiments, pretreating by sieving and/or sonicating, results in a loading efficiency of at least 80%, and preferably, at least 90% in conventional chewing gums.

In certain embodiments, at least 60%, and preferably, at least 80% of the MBE present in the oral composition is released into the oral cavity of a consumer after chewing the oral composition for at least 10 minutes, or at least 20 minutes. In certain embodiments, at least 60% and preferably, at least 90% of the LAE present in the oral composition is released into the oral cavity of a consumer after chewing the oral composition for at least 10 minutes, or at least 20 minutes.

Thus, in one particular preferred embodiment, the present disclosure is directed to a method of making a coated oral composition. The method comprises pretreating MBE and LAE to form a preblend mixture, adding the preblend mixture to a coating syrup, and applying the coating syrup to an oral composition to produce the coated oral composition. The MBE and LAE may be pretreated by sieving the MBE and LAE prior to addition to the coating syrup; sonicating the MBE and LAE prior to addition to the coating syrup; blending the MBE and LAE with one or more organoleptic components prior to addition to the coating syrup; pre-dissolving the MBE and LAE in a flavoring agent, glycerol, and/or medium-chain triglyceride (MCT) oil; or combinations thereof.

In still other embodiments, the present disclosure is directed to a method of making a chewing gum composition. The method comprises pretreating MBE and LAE to form a preblend mixture, and forming the chewing gum composition from the preblend mixture. The MBE and LAE may be pretreated by sieving the MBE and LAE; sonicating the MBE and LAE; blending the MBE and LAE with a powdered gum base; pre-dissolving the MBE and LAE in a flavoring agent, glycerol, and/or medium-chain triglyceride (MCT) oil; or combinations thereof.

In certain embodiments, the amount of MBE and LAE included in the preblend mixture is sufficient to provide a synergistic inhibition of the formation of plaque biofilm by salivary bacteria in the oral cavity of a consumer of the oral composition. In particular embodiments, the MBE and LAE are added to the preblend mixture in a weight ratio of from about 16:1 to about 4:1, including from about 16:1 to about 8:1, or from about 8:1 to about 4:1.

In some embodiments, the MBE and LAE are pretreated by blending the MBE and LAE with one or more organoleptic components prior to addition to the oral composition. In particular embodiments, the preblend mixture is added to a coating syrup and applied to the oral composition. Suitable organoleptic components include, but are not limited to, a flavoring agent, a cooling agent, a heating agent, a mouthfeel agent, a tingling agent, a sweetening agent, a souring agent, a salivating agent, a bittering agent, a teeth whitening agent, an anti-cavity agent, a breath freshening agent, an audible agent, and combinations thereof. In still other embodiments, the MBE and LAE are pretreated by blending the MBE and LAE with a powdered gum base prior to addition to a gum composition (e.g., a compressed chewing gum composition). In still other embodiments, the MBE and LAE are pretreated by pre-dissolving the MBE and LAE in a flavoring agent, glycerol, and/or medium-chain triglyceride (MCT) oil prior to addition to a gum composition.

In some embodiments, the MBE and LAE are combined and sieved, sonicated or both prior to blending with the one or more organoleptic components, or the powdered gum base. In another embodiment, the MBE and LAE are blended with the organoleptic components or the powdered gum base, and the resulting mixture sieved, sonicated or both. Preferably, a mixture of MBE and LAE is sieved then sonicated prior to blending with the organoleptic components or the powdered gum base.

Any of the oral compositions disclosed herein may be prepared using the methods described herein. In particular embodiments, the oral composition prepared according to the method of the disclosure is selected from the group consisting of chewing gums, confections, mints, tablets, beads, and lozenges. Preferably, the oral composition is a chewing gum or a mint. More preferably, the oral composition is a chewing gum, such as a coated chewing gum, a center-filled chewing gum, or a coated center-filled chewing gum. Preferably, the gum is a coated chewing gum.

Methods of Use

As discussed herein, it has surprisingly been discovered that MBE in combination with LAE is synergistically effective at inhibiting the formation of plaque biofilm by salivary bacteria. This combination thus greatly improves and facilities the inhibition of plaque biofilm by salivary bacteria in the oral cavity of a consumer. Incorporating the combination of an effective amount of MBE and LAE into an oral composition can thus provide an oral composition that inhibits the formation of plaque biofilm by salivary bacteria. The oral compositions of the present disclosure may also be effective for use in the removal of existing plaque.

Thus, in another aspect, the present disclosure is directed to inhibiting the formation of plaque biofilm in the oral cavity of a consumer, and in particular, on teeth. The method comprises contacting a composition of the present disclosure with the oral cavity. Preferably, the consumer is a mammal. The mammal may be a human or a non-human animal. Most preferably, the mammal is human. The composition may be contacted with the oral cavity for at least 10 minutes, or at least about 20 minutes.

The invention is illustrated by, but not limited to, the following Examples.

EXAMPLES

Example 1: In Vitro Biofilm Analysis

The effect of various concentrations of MBE and LAE on biofilm formation was evaluated in vitro.

In Vitro Biofilm Testing

Biofilms were prepared and tested by a modified method from Guggenheim (Guggenheim B., Gierstein E., Schupbach P, Shapiro S., 2001. "Validation of an in vitro biofilm model of supragingival plaque" *Journal Dental Research* 80:363-370), which is herein incorporated by reference. Briefly, biofilms were grown by incubating salivary bacteria with saliva-treated hydroxyapatite (HA) discs in sterile 24 well cell culture plates. Using media supplemented with saliva (25% total volume), and transferring discs frequently during the growth phase, encouraged growth of a dental plaque-like biofilm. This was developed for up to 72 hours. The biofilm was exposed to the test compositions (set forth in Table 1) three times a day, for five minutes, on days two and three of the experiment. Biofilm was quantified turbidometrically and by spectrophometric absorption at 600 nm.

The number of CFU for each biofilm was determined as follows. After vigorous shaking, 0.1 ml of the liquid from each biofilm cell was pipetted into 10 ml reverse osmosis (RO) $H_2O$ (100× dilution). The 100× dilution was shaken, and 0.1 ml was pipetted into 10 ml RO $H_2O$ (10,000× dilution). The 10,000× dilution was shaken, and 0.1 ml was pipetted into 10 ml RO $H_2O$ (10,000,000× dilution). 500 µL of each of the dilutions was deposited in a spiral via WASP II autoplater onto CDC agar. The plates were incubated for 48 hours at 37° C. in anaerobic conditions. After the growth period, the number of colonies of bacteria growing on each plate were counted. The initial concentration of total oral bacteria was estimated to be about 1~2×10$^6$ CFU/ml.

The $IC_{40}$ of MBE was determined, and was used as a positive control concentration.

Results

The results of the in vitro biofilm assay are set forth in Table 1.

TABLE 1

In vitro biofilm assay results

| Ingredient | Concentration tested (ppm) | % Inhibition |
|---|---|---|
| MBE** | 1000 | 91.00 |
| | 250 | 92.00 |
| | 125 | 81.00 |
| | 64 | 68.00 |
| | 32 | 35.00 |
| | 16 | 30.00 |
| Listerine | 1% | 71.00 |
| LAE* | 1000 | 82.00 |
| LAE* + MBE** | 100 + 40 | 84.42 |

*LAE is LAE-CF from Vedeqsa of Barcelona, Spain (99% purity)
**MBE from Honsea Sunshine Biotech, Ltd., Guangzhou, China (95% magnolol and 5% honokiol)

The percent inhibition of the LAE alone was not better than the positive control, but the combination of LAE and MBE had improved inhibition as compared to the positive control.

Example 2: In Vivo Biofilm Analysis

The effect of chewing gums comprising various concentrations of MBE and LAE on plaque formation and salivary bacteria was evaluated. Chewing gum formulations tested were as follows:

Formulation A: control gum (Winterfresh);
Formulation B: coated gum comprising MBE (5.3 mg of MBE delivery/serving; 1.2% by weight in gum coating);
Formulation C: coated gum comprising MBE+LAE (7.7 mg of MBE+9.0 mg of LAE delivery/serving; 1.2% by weight MBE in gum coating);
Formulation D: MBE suck-chew gum (9.6 mg of MBE delivery/serving; 1.2% by weight in gum coating). The suck-chew gum was consumed by having the subjects suck the gum for 2 minutes followed by chewing.

Plaque Screen

Twelve (12) subjects consumed 5 servings of gum in 5 separated doses a day for 4 days (Mon-Thu) for 20 minutes. After the end of each leg (Day 5, (Friday afternoon)), the subjects consumed one additional serving of gum. Plaque was disclosed and digital photographs and quantitative light-induced fluorescence (QLF) images of the labial surfaces of the anterior teeth (canine to canine, Mn, Mx) of each subject were taken (visualizing with use of stains with a dye). The subjects were provided with a further prophylaxis (professional dental cleaning) and then underwent a 9 day washout during which they resume their normal oral hygiene procedures using a provided toothbrush and paste. The subjects were asked to present the following Monday for the next phase of the experiment. This was repeated until each subject had used all oral composition formulations.

Microbiological Analysis

The saliva samples (from both day 1 and day 5) were collected in ice containers and immediately transported to a microbiology laboratory for analysis. The number of bacteria in each sample was determined by serial dilution in phosphate buffered saline and plating onto selective and non-selective solid media, and incubation under anaerobic conditions at 37° C. Blood agar and *Mitis salivarius* agar was used to determine the total number of salivary bacteria, and *Streptococcus* spp. Blood agar plates were re-examined after 7 days of anaerobic incubation to determine the number of black pigmented anaerobic organisms.

Data was analyzed by analysis of variance with pair-wise post-hoc comparisons. The microbiology data was logarithmically transformed for analysis. For these screeners, the alpha level was set at 15% (i.e., $p<0.15$).

Results

Three gum formulas (Formulations B, C, and D) and a control (Formulation A) were tested against human in vivo plaque re-growth. The results are set forth in FIGS. 1A and 1B and Tables 2 and 3.

TABLE 2

Statistical difference between groups (QLF)

|  | Red fluorescence | ΔR |
|---|---|---|
| A vs. B | 0.672 | 0.428 |
| A vs. C | 0.051 | 0.159 |
| A vs. D | 0.660 | 0.790 |
| B vs. C | 0.015 | 0.010 |
| B vs. D | 0.844 | 0.147 |
| C vs. D | 0.033 | 0.154 |

TABLE 3

Microbiology Test Results

| | Day 5 | | | | | | Shift | | | | | |
|---|---|---|---|---|---|---|---|---|---|---|---|---|
| | FAA | | MSA | | BP | | FAA | | MSA | | BP | |
| | log cfu | p (vs. A) | log cfu | p (vs. A) | log cfu | p (vs. A) | log cfu | p (vs. A) | log cfu | p (vs. A) | log cfu | p (vs. A) |
| A | 7.77 | — | 6.77 | — | 5.15 | — | −0.15 | — | −0.17 | — | 0.75 | — |
| B | 7.77 | 0.490 | 6.51 | 0.221 | 4.86 | 0.247 | −0.12 | 0.445 | −0.26 | 0.350 | 0.73 | 0.488 |
| C | 7.45 | 0.046 | 6.29 | 0.109 | 4.41 | 0.100 | −0.34 | 0.136 | −0.31 | 0.398 | −0.15 | 0.161 |
| D | 7.72 | 0.357 | 6.56 | 0.321 | 4.73 | 0.203 | −0.12 | 0.451 | −0.18 | 0.439 | −0.02 | 0.140 |

Day 5 denotes mean cfu value at the end of each treatment.
Shift denotes average cfu shift of all subjects from day 1 to day 5 of each treatment.
FAA: Fastidious Anaerobe Agar for total anaerobes.
MSA: *Mitis salivarius* agar for *Streptococcus* spp.
BP: Black Pigmented.
P values were determined using 1 tail paired t-test.

Figure 1B:
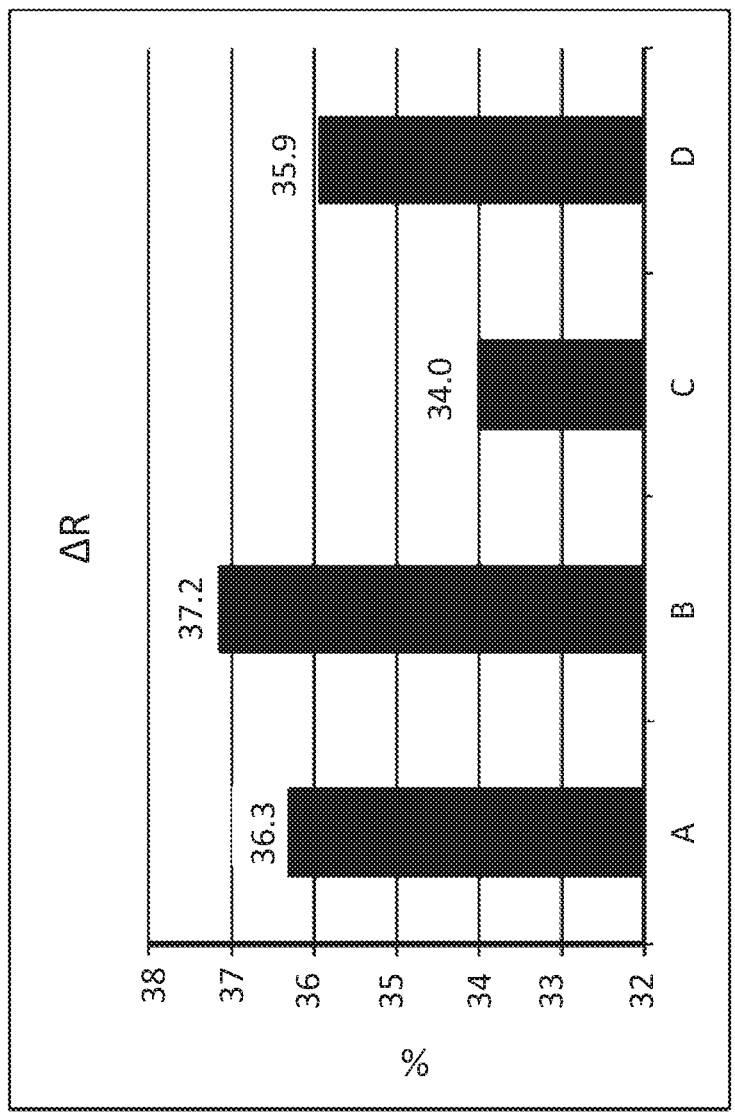

As can be seen in FIGS. 1A and 1B and Table 2, only the MBE+LAE leg (Formulation C) showed significant reduction in plaque area by ca. 30% ($p=0.05$), as detected by QLF (red fluorescence). Formulation C had higher efficacy than MBE alone (Formulations B and D) and the control (Formulation A), even though the MBE delivery amount was lower than that of Formulation D. As can be seen from Table 3, the microbiology results showed a statistically significant change for FAA cfu at Day 5 (0.5 log reduction, $p=0.04$).

These results demonstrate that oral compositions comprising a combination of MBE and LAE result in a reduced formation of plaque in vivo, as compared to oral compositions comprising MBE in the absence of LAE.

Example 3: Synergistic Effect of MBE and LAE in Preventing Plaque Biofilm Formation In this example, the effect of MBE and LAE on preventing plaque biofilm formation by salivary bacteria was evaluated.

80 ml of saliva was collected from 4 donors and centrifuged at 3800 rpm to remove food debris. 15 ml supernatant was removed and mixed with an equal volume of 1×PBS. The mixture was then filter sterilized to collect saliva proteins that were used to precoat suspended pegs in the lid of the Calgary device for 3 hours. Meanwhile, the remaining saliva was centrifuged at 10,000 rpm to collect bacteria for biofilm inoculum. After centrifugation, the pellet was resuspended to an $OD_{600}$ of 0.05 and premixed with defined concentrations of LAE-CF (99% purity, from Vedeqsa), MBE and a combination of the two actives at predetermined ratios. The actives and inoculum were added to the saliva precoated pegs and incubated overnight for at least 16 hours to allow for biofilm formation. Controls included growth (no actives) and media only (no bacteria).

Results

The results are shown in Table 4 below. The efficacy of the LAE and MBE synergistic effects are shown in the minimal biofilm inhibitory concentrations (MBIC) and fractional biofilm inhibitory concentration (FBIC) for the two actives. The FBIC was calculated according to the following formula:

$$FBIC = [Q_A/Q_a + Q_B/Q_b]$$ where $Q_A$=the MBIC of component A combined with component B.

$Q_a$=the MBIC of component A alone.

$Q_B$=the MBIC of component B combined with component A.

$Q_b$=the MBIC of component B alone.

If the FBIC<1, components A and B are synergistic; if 1≤FBIC≤2, components A and B are additive; and if 2<FBIC, components A and B are antagonistic. The lower the FBIC value (when FBIC<1), the stronger the synergistic effect between the two components.

Surprisingly, the synergistic activity for inhibiting biofilm formation was observed for MBE:LAE ratios of 4:1, 8:1 and 16:1. The combination of MBE and LAE was in the range of 1.3 to 1.8 fold more effective than MBE or LAE alone. In particular and very surprisingly, high efficacy was observed for the MBE:LAE ratio of 16:1, with an FBIC of 0.564, representing nearly 2 fold more potency than either MBE or LAE alone. The small amount of LAE relative to MBE will permit a more cost effective and efficient preparation of different oral compositions.

TABLE 4

Synergistic effect of MBE and LAE on inhibition of biofilm formation by salivary bacteria

| Sample (ppm) | MBE | LAE-CF | MBE/LAE-CF 4:1 | MBE/LAE-CF 8:1 | MBE/LAE-CF 16:1 |
|---|---|---|---|---|---|
| MBIC | 250 | 125 | 125/32 | 125/16 | 125/8 |
| FBIC | 1 | 1 | 0.756 | 0.628 | 0.564 |

Example 4: Loading Efficiency and Release of LAE from Gum

In this example, the loading efficiency and release of LAE from gum was evaluated.

For evaluating release of LAE from pellet gum, samples were formulated with LAE-CF in peppermint gum. Samples were chewed for 20 minutes by volunteers. The bolus of the gum was stored and frozen until analysis. The gum bolus from 6 chewers and unchewed LAE gum was tested via HPLC and compared to determine chew-out/release from gum. Table 5 shows the recovery and release of LAE from the gum center.

TABLE 5

Loading Efficiency of LAE from Peppermint Flavored Gum Center

| Sample | Formulation input of LAE | HPLC analytical result of LAE | Loading efficiency of LAE | Release of LAE after 20 min of chew |
|---|---|---|---|---|
| Peppermint stick with 0.2% LAE | 0.20% | 0.169% | 85% | 25.4% |
| Peppermint pellet with 0.075% LAE | 0.075% | 0.076% | 100% | 17% |

As can be seen from Table 5, about 85%~100% of the LAE that was added during formulation was present in the gum samples, indicating that only about 0-15% of the LAE added during formulation was lost during formulation. Of the LAE present in the gum samples, 25.4% of the LAE was released from a stick gum; and 17% of the LAE was released from a pellet gum after 20 minutes of chew.

Example 5: Loading Efficiency and Release of MBE and LAE from Gum

The following gum formulations were used to evaluate the loading efficiency and release of MBE or MBE plus LAE from gum.

| ID | Composition | Loading |
|---|---|---|
| 1 | Placebo gum | Wintergreen flavor (no MBE or LAE) |
| 2 | MBE 1.2% by wt. in coating | 12 mg/serving |
| 3 | MBE 1.2% by wt. in coating consumed as suck-chew | 12 mg/serving |
| 4 | MBE 1.2% by wt. in coating and LAE 1.5% by wt. in coating | MBE: 12 mg/serving, LAE: 15 mg/serving |

For composition 3 (MBE-suck), the gum pellet was consumed by sucking the pellet for 2 minutes to completely dissolve the coating layer, followed by chewing for 8 minutes. Compositions 1, 2, and 4, were consumed by regular chewing for 10 minutes. The amount of MBE and LAE before (load) and after (release) chewing was determined. The results are set forth in Table 6.

TABLE 6

Loading and Delivery Results (in mg)

| Name | ID | MBE load | MBE release | LAE load | LAE release |
|---|---|---|---|---|---|
| Ctrl | 1 | 0.00 | 0.01 | | |
| MBE | 2 | 7.56 | 5.32 | | |
| MBE + LAE | 3 | 10.41 | 7.71 | 11.70 | 9.00 |
| MBE-suck | 4 | 10.32 | 9.61 | | |

As can be seen from Table 6, release of MBE and LAE is higher when formulated in the coating of a chewing gum. In addition, the suck-chew method further improves the release of MBE.

Example 6: Coated Chewing Gum

In this example, coating compositions containing MBE or MBE and LAE are prepared. The coating compositions can be used to prepare coated oral compositions containing MBE and LAE.

A coating composition is prepared according to the formula set forth in Table 7.

TABLE 7

| Coating composition | |
|---|---|
| Ingredient | Weight % |
| Polyol | 63.83 |
| Water | 22.22 |
| 40% gum tahla | 12.39 |
| Color | 0.42 |
| High potency sweetener | 0.42 |
| Cooling agent | 0.72 |
| Total | 100.00 |

MBE coating composition: 3.75 g of MBE is added to 300 g of the coating composition in Table 7. The resulting coating composition comprises 1.25% by weight of MBE. The MBE coating composition may be applied to oral compositions, such as chewing gum, in an amount sufficient to provide a concentration of MBE of 12 mg/serving.

MBE/LAE coating composition: 3.75 g of MBE and 4.65 g of LAE are added to 300 g of the coating composition in Table 7. The resulting coating composition comprises 1.25% by weight of MBE and 1.55% by weight of LAE. The MBE/LAE coating composition may be applied to oral compositions, such as chewing gum, in an amount sufficient to provide a concentration of MBE of 12 mg/serving and a concentration of LAE of 15 mg/serving.

Example 7: Effect of Chewing Gum Comprising MBE and LAE on Acid Production and Regrowth of Human Supragingival Plaque Bacteria In this example, the effect of MBE and LAE on the regrowth and glycolysis of human supragingival plaque, and the effectiveness of chewing gum as a delivery mechanism, was evaluated using the Plaque Glycolysis and Regrowth Method (PGRM).

Six adults ages 18-65 years old (five females, one male) of all race and gender participated in the study. Participants refrained from oral hygiene the night before and the morning of the test visit. Their overnight supragingival plaque was collected (upper and lower left) before chewing a gum sample (pre-treatment sample, "pre"). Participants then chewed one of the gum samples for 10 min, and their upper and lower right plaque samples were collected 20 min after chewing (post-treatment samples, "post"). All plaque samples before and after chewing were tested in vitro for their ability to grow and produce acid using the PGRM, as described in White et al., *J. Clin. Dent.* 6 [special issue]: 59-70, 1995, which is herein incorporated by reference. Their ability to form in vitro biofilm may was also tested.

Treatment Groups

The gum samples evaluated in this test were: a) a gum base control; b) an experimental gum comprising both MBE and LAE ("MBE gum"); and c) a gum without MBE or LAE ("control gum"). The MBE gum (3000 mg serving size, administered as two 1500 mg pellets) was identical to the control gum, except comprised 15 mg (0.5 wt %) MBE and 2 mg (0.067 wt %) LAE per serving.

PGRM—Glycolysis Activity Measurements

Figure 2:
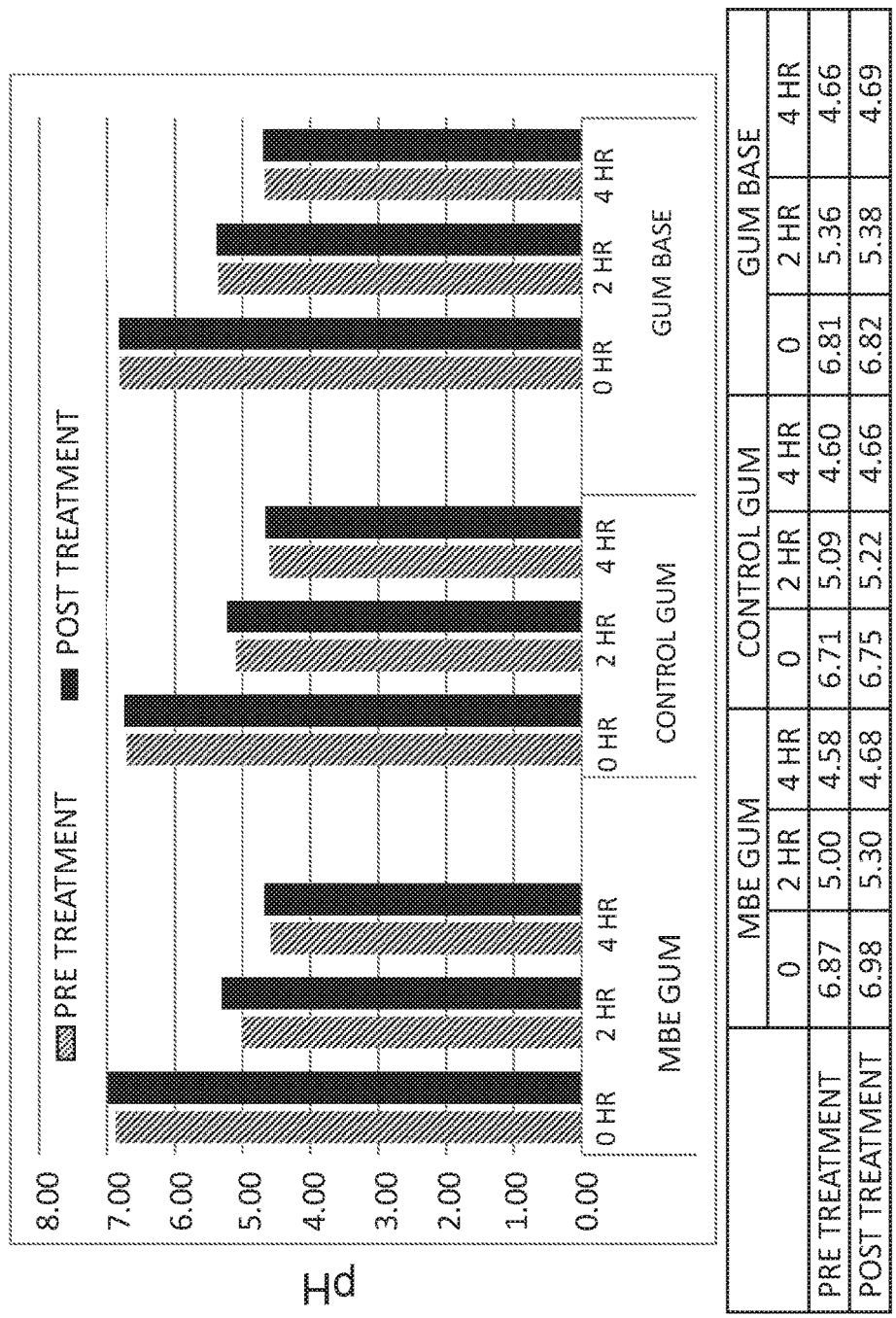
FIG. 2 is a graph depicting the effect of chewing gum on the acid production of plaque bacteria. Plaque bacteria was collected before ("pre treatment") and after ("post treatment") chewing of an MBE/LAE containing gum ("MBE gum"), a control gum containing no MBE or LAE ("control gum"), or a gum base containing no MBE or LAE.
Figure 3:
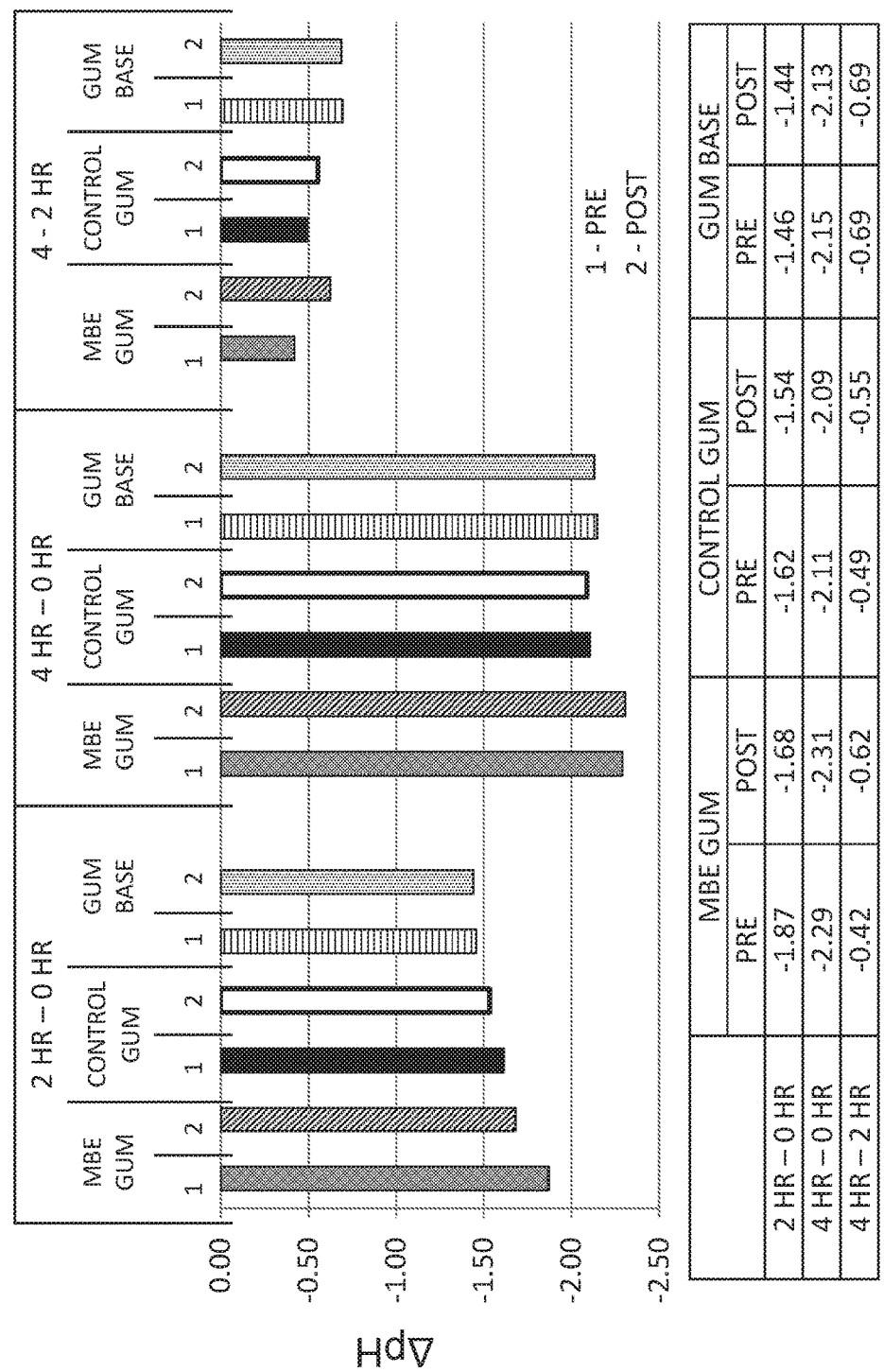
FIG. 3 is a graph depicting the change in acid production (represented as difference in pH, "$\Delta$pH") of plaque bacteria 2 and 4 hours after chewing ("post") of an MBE/LAE containing gum ("MBE gum"), a control gum containing no MBE or LAE ("control gum"), or a gum base containing no MBE or LAE. The change in acid production over time of plaque bacteria collected before ("pre") chewing is also depicted.

The in vivo treated plaque samples ("post") were compared to the untreated plaque samples ("pre") for glycolytic activity. The pre- and post-treatment plaque samples were dispersed in buffer, and the optical density (OD) of the samples (measured at 600 nm) was adjusted to 0.20±0.01 with addition of 0.03% buffer (tryptic soy broth, "TSB") solution to obtain normalized biomass plaques. One mL of the normalized biomass plaques was pipetted into a 2 mL Eppendorf vial, and bacterial metabolism was initiated by the addition of 50 μL of a 40% sucrose stock solution. The normalized plaques were subsequently incubated at 37° C. and 120 rpm agitation. Acid production following 2 and 4 hours of incubation was measured by pH change in the suspension buffer. The results are set forth in Tables 8-10, and in FIGS. 2 and 3.

TABLE 8

Effect of Chewing MBE Gum (MBE and LAE) on Acid Production of Human Supragingival Plaque Bacteria

| | pH data | | | | | | ΔpH | | | | | |
|---|---|---|---|---|---|---|---|---|---|---|---|---|
| | Pre | | | Post | | | Pre | | | Post | | |
| | 0 | 2 hr | 4 hr | 0 | 2 hr | 4 hr | 2-0 hr | 4-0 hr | 4-2 hr | 2-0 hr | 4-0 hr | 4-2 hr |
| 1 | 6.63 | 4.97 | 4.49 | 6.85 | 6.18 | 4.84 | −1.66 | −2.14 | −0.49 | −0.67 | −2.01 | −1.35 |
| 2 | 7.08 | 5.46 | 4.86 | 7.07 | 5.57 | 4.88 | −1.63 | −2.22 | −0.60 | −1.50 | −2.19 | −0.69 |
| 3 | 7.26 | 4.99 | 4.52 | 7.30 | 5.18 | 4.64 | −2.26 | −2.74 | −0.47 | −2.12 | −2.66 | −0.54 |
| 4 | 6.77 | 4.75 | 4.34 | 6.83 | 4.98 | 4.43 | −2.02 | −2.43 | −0.41 | −1.85 | −2.40 | −0.55 |
| 5 | 6.58 | 4.93 | 4.64 | 6.71 | 4.93 | 4.63 | −1.65 | −1.94 | −0.29 | −1.79 | −2.09 | −0.30 |
| 6 | 6.92 | 4.91 | 4.64 | 7.14 | 4.98 | 4.65 | −2.01 | −2.28 | −0.27 | −2.17 | −2.49 | −0.33 |
| avg | 6.87 | 5.00 | 4.58 | 6.98 | 5.30 | 4.68 | −1.87 | −2.29 | −0.42 | −1.68 | −2.31 | −0.62 |

TABLE 9

Effect of Chewing Control Gum (No MBE/LAE) on Acid Production of Human Supragingival Plaque Bacteria

| | pH data | | | | | | ΔpH | | | | | |
|---|---|---|---|---|---|---|---|---|---|---|---|---|
| | Pre | | | Post | | | Pre | | | Post | | |
| | 0 | 2 hr | 4 hr | 0 | 2 hr | 4 hr | 2-0 hr | 4-0 hr | 4-2 hr | 2-0 hr | 4-0 hr | 4-2 hr |
| 1 | 6.48 | 5.41 | 4.85 | 7.09 | 6.24 | 5.24 | −1.07 | −1.63 | −0.56 | −0.85 | −1.85 | −1.00 |
| 2 | 6.68 | 4.96 | 4.62 | 6.03 | 4.94 | 4.54 | −1.72 | −2.06 | −0.34 | −1.09 | −1.49 | −0.40 |
| 3 | 7.22 | 4.65 | 4.21 | 7.43 | 4.76 | 4.27 | −2.57 | −3.01 | −0.44 | −2.67 | −3.16 | −0.49 |
| 4 | 6.80 | 5.68 | 4.62 | 6.84 | 5.47 | 4.59 | −1.13 | −2.19 | −1.06 | −1.37 | −2.25 | −0.88 |
| 5 | 6.79 | 4.87 | 4.66 | 6.80 | 4.99 | 4.74 | −1.92 | −2.13 | −0.22 | −1.82 | −2.06 | −0.24 |
| 6 | 6.27 | 4.98 | 4.64 | 6.34 | 4.92 | 4.61 | −1.29 | −1.63 | −0.34 | −1.42 | −1.73 | −0.31 |
| avg | 6.71 | 5.09 | 4.60 | 6.75 | 5.22 | 4.66 | −1.62 | −2.11 | −0.49 | −1.54 | −2.09 | −0.55 |

TABLE 10

Effect of Chewing Non-Flavored Gum Base on Acid Production of Human Supragingival Plaque Bacteria

| | pH data | | | | | | ΔpH | | | | | |
|---|---|---|---|---|---|---|---|---|---|---|---|---|
| | Pre | | | Post | | | Pre | | | Post | | |
| | 0 | 2 hr | 4 hr | 0 | 2 hr | 4 hr | 2-0 hr | 4-0 hr | 4-2 hr | 2-0 hr | 4-0 hr | 4-2 hr |
| 1 | 6.76 | 5.08 | 4.48 | 6.81 | 5.47 | 4.72 | −1.68 | −2.28 | −0.60 | −1.34 | −2.09 | −0.75 |
| 2 | 7.22 | 5.28 | 4.68 | 7.12 | 5.46 | 4.77 | −1.95 | −2.55 | −0.60 | −1.66 | −2.35 | −0.69 |
| 3 | 6.99 | 5.18 | 4.58 | 6.96 | 5.46 | 4.74 | −1.81 | −2.41 | −0.60 | −1.50 | −2.22 | −0.72 |
| 4 | 6.51 | 5.59 | 4.84 | 6.62 | 5.46 | 4.79 | −0.92 | −1.67 | −0.75 | −1.16 | −1.83 | −0.67 |
| 5 | 6.76 | 5.48 | 4.66 | 6.75 | 5.14 | 4.50 | −1.28 | −2.10 | −0.82 | −1.61 | −2.25 | −0.64 |
| 6 | 6.64 | 5.54 | 4.75 | 6.69 | 5.30 | 4.65 | −1.10 | −1.89 | −0.79 | −1.39 | −2.04 | −0.66 |
| avg | 6.81 | 5.36 | 4.66 | 6.82 | 5.38 | 4.69 | −1.46 | −2.15 | −0.69 | −1.44 | −2.13 | −0.69 |

Inhibiting the ability of plaque bacteria to metabolize sugar to acids is one measure of the effectiveness of antimicrobial agents, with a reduction in acid production following treatment being evidence of an antimicrobial effect. As can be seen from the results set forth in Tables 8-10 and FIGS. 2 and 3, the pH for the MBE gum (containing MBE and LAE) treated plaque sample was 0.3 pH units higher after two hours, as compared to the untreated ("pre") control plaque sample, indicating a reduced acid-forming activity of the bacteria exposed to this gum. The results thus show a positive trend in reducing acid production up to 2 hours after chewing of the MBE gum for 10 minutes. No statistically significant trend in reduction of acid production was seen with the gum base and control gum.

PGRM—Plaque Regrowth Activity

Figure 4:
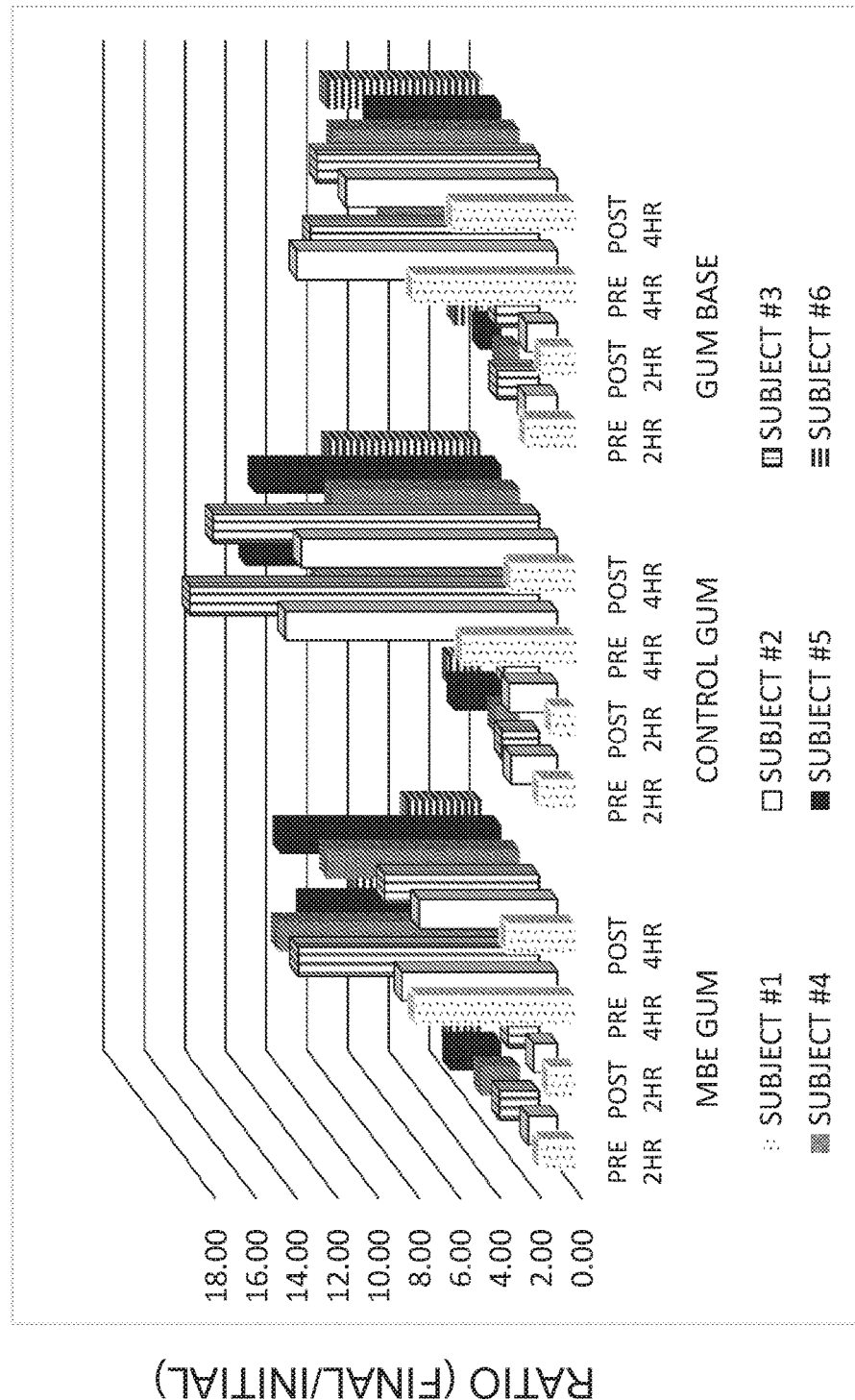
FIG. 4 is a graph depicting the effect of chewing gums on the regrowth of plaque bacteria (expressed as regrowth ratios, $OD_{final/initial}$) in six test subjects 2 and 4 hours after chewing ("post") of an MBE/LAE containing gum ("MBE gum"), a control gum containing no MBE or LAE ("control gum"), or a gum base containing no MBE or LAE. The regrowth over time of plaque bacteria collected before ("pre") chewing is also depicted.
Figure 5:
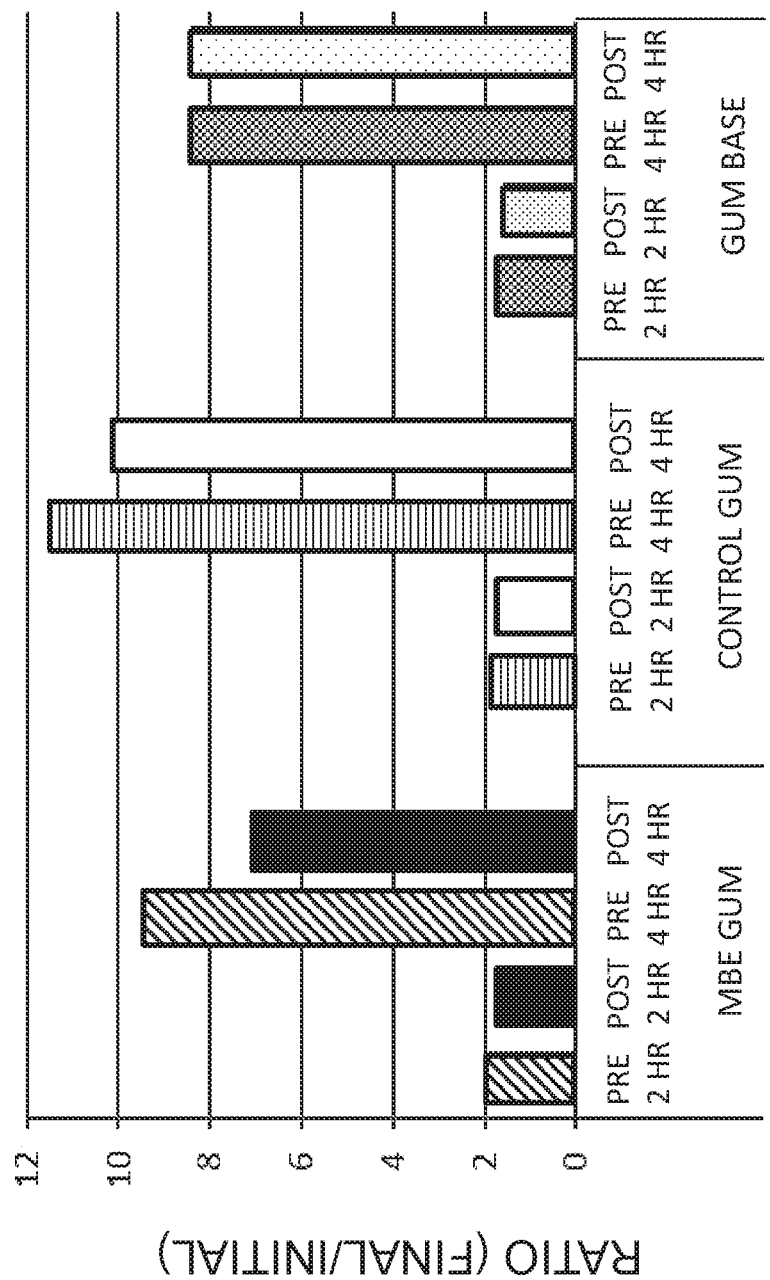
FIG. 5 is a graph depicting the average regrowth ratios of plaque bacteria 2 and 4 hours after chewing ("post") of an MBE/LAE containing gum ("MBE gum"), a control gum containing no MBE or LAE ("control gum"), or a gum base containing no MBE or LAE. The regrowth over time of plaque bacteria collected before ("pre") chewing is also depicted.

The effects of MBE and LAE on plaque growth were determined by assessing the bacterial regrowth of normalized plaque samples in aerobic media. A 300 μL aliquot of the dispersed plaque from the glycolysis vials prepared above was transferred to a separate 2 mL Eppendorf vial containing 0.5 mL of 6% (w/w) BBL TSB (pH 7.1±0.2) along with 100 μL of sterile water. Bacterial growth in the broth was accelerated by the addition of 50 μL of stock 40% sucrose solution. Following sample preparation, the initial optical density of the plaque dispersion was measured at 600 nm in a 3 mL disposable curvette in a spectrometer. Samples were incubated in 2 mL Eppendorf tubes at 37° C. at 1200 rpm. Plaque samples were incubated for 4 hours, and measured for optical density (600 nm) at 2 and 4 hours following homogenization with a pellet mixer. The results are set forth in Tables 11-14 and FIGS. 4 and 5. Regrowth results are reported as the final plaque dispersion turbidity ($OD_{600}$).

TABLE 11

Effect of Chewing MBE Gum (MBE and LAE) on Regrowth ($OD_{600}$) of Human Supragingival Plaque Bacteria

| | Pre | | | Post | | |
|---|---|---|---|---|---|---|
| Subject | 0 hr | 2 hr | 4 hr | 0 hr | 2 hr | 4 hr |
| #1 | 0.033 | 0.059 | 0.262 | 0.030 | 0.040 | 0.100 |
| #2 | 0.057 | 0.084 | 0.450 | 0.055 | 0.064 | 0.376 |
| #3 | 0.052 | 0.100 | 0.623 | 0.054 | 0.080 | 0.407 |
| #4 | 0.047 | 0.085 | 0.530 | 0.044 | 0.069 | 0.439 |
| #5 | 0.066 | 0.169 | 0.640 | 0.064 | 0.166 | 0.705 |
| #6 | 0.067 | 0.113 | 0.421 | 0.075 | 0.088 | 0.279 |
| avg | 0.054 | 0.102 | 0.488 | 0.054 | 0.084 | 0.384 |

TABLE 12

Effect of Chewing Control Gum on Regrowth ($OD_{600}$) of Human Supragingival Plaque Bacteria

| | Pre | | | Post | | |
|---|---|---|---|---|---|---|
| Subject | 0 hr | 2 hr | 4 hr | 0 hr | 2 hr | 4 hr |
| #1 | 0.029 | 0.052 | 0.162 | 0.021 | 0.025 | 0.067 |
| #2 | 0.057 | 0.130 | 0.762 | 0.057 | 0.134 | 0.712 |
| #3 | 0.056 | 0.100 | 0.952 | 0.056 | 0.095 | 0.895 |
| #4 | 0.032 | 0.041 | 0.341 | 0.025 | 0.036 | 0.261 |
| #5 | 0.064 | 0.151 | 0.798 | 0.063 | 0.149 | 0.763 |
| #6 | 0.044 | 0.074 | 0.408 | 0.053 | 0.052 | 0.403 |
| avg | 0.047 | 0.091 | 0.570 | 0.046 | 0.082 | 0.517 |

TABLE 13

Effect of Chewing Non-Flavored Gum Base on Regrowth (OD$_{600}$) of Human Supragingival Plaque Bacteria

| Subject | Pre | | | Post | | |
|---|---|---|---|---|---|---|
| | 0 hr | 2 hr | 4 hr | 0 hr | 2 hr | 4 hr |
| #1 | 0.039 | 0.095 | 0.313 | 0.030 | 0.051 | 0.182 |
| #2 | 0.066 | 0.104 | 0.839 | 0.061 | 0.093 | 0.634 |
| #3 | 0.065 | 0.133 | 0.730 | 0.065 | 0.138 | 0.708 |
| #4 | 0.033 | 0.033 | 0.221 | 0.035 | 0.051 | 0.321 |
| #5 | 0.060 | 0.065 | 0.301 | 0.063 | 0.087 | 0.406 |
| #6 | 0.064 | 0.092 | 0.420 | 0.058 | 0.078 | 0.442 |
| avg | 0.054 | 0.087 | 0.471 | 0.052 | 0.083 | 0.449 |

TABLE 14

Regrowth Ratios (OD$_{final}$/OD$_{initial}$)

| | MBE Gum | | | | Control Gum | | | | Gum Base | | | |
|---|---|---|---|---|---|---|---|---|---|---|---|---|
| | 2 hr | | 4 hr | | 2 hr | | 4 hr | | 2 hr | | 4 hr | |
| subject | pre | post | Pre | post | pre | post | Pre | post | pre | post | Pre | post |
| #1 | 1.79 | 1.36 | 7.92 | 3.39 | 1.79 | 1.19 | 5.59 | 3.19 | 2.44 | 1.70 | 8.03 | 6.07 |
| #2 | 1.45 | 1.17 | 7.65 | 6.83 | 2.28 | 2.37 | 13.35 | 12.60 | 1.58 | 1.52 | 12.80 | 10.40 |
| #3 | 1.92 | 1.50 | 11.83 | 7.60 | 1.80 | 1.70 | 17.14 | 15.99 | 2.05 | 2.11 | 11.22 | 10.90 |
| #4 | 1.91 | 1.59 | 11.88 | 9.50 | 1.23 | 1.29 | 9.97 | 9.26 | 1.00 | 1.46 | 6.70 | 9.17 |
| #5 | 2.55 | 2.54 | 9.72 | 10.85 | 2.37 | 2.36 | 12.56 | 12.09 | 1.08 | 1.38 | 5.02 | 6.44 |
| #6 | 1.69 | 1.17 | 6.28 | 3.72 | 1.68 | 0.98 | 9.27 | 7.60 | 1.43 | 1.36 | 6.67 | 7.68 |
| avg | 1.89 | 1.55 | 9.22 | 6.98 | 1.86 | 1.65 | 11.31 | 10.12 | 1.60 | 1.59 | 8.41 | 8.44 |
| SD* | 0.37 | 0.51 | 2.32 | 3.01 | 0.42 | 0.60 | 3.96 | 4.46 | 0.56 | 0.29 | 2.99 | 2.03 |

*Standard deviation

As can be seen from these results, there was a positive trend in reducing short-term plaque bacteria regrowth of up to 4 hours after chewing the MBE gum (containing MBE and LAE) for 10 minutes, while the control gum and gum base did not inhibit plaque bacteria regrowth. These results suggest that chewing gum may serve as an effective oral delivery system of antimicrobial agents for short-term plaque control.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An oral composition for inhibiting the formation of plaque biofilm by salivary bacteria in an oral cavity of a consumer, the composition comprising magnolia bark extract (MBE) and L-arginine, N$^\alpha$-lauroyl-ethyl ester (LAE), wherein the oral composition comprises the MBE and LAE in amounts that provide a synergistic inhibition of the formation of plaque biofilm in the oral cavity.

2. The oral composition of claim 1, wherein the weight ratio of MBE to LAE is from about 16:1 to about 4:1.

3. The oral composition of claim 1, wherein the oral composition comprises from about 1 to about 20 mg of MBE.

4. The oral composition of claim 1, wherein the oral composition comprises from about 1 to about 10 mg of MBE.

5. The oral composition of claim 1, wherein the oral composition comprises from about 1 to about 20 mg of LAE.

6. The oral composition of claim 1, wherein the oral composition is selected from the group consisting of a chewing gum, a confection, a mint, a tablet, a bead, and a lozenge.

7. The oral composition of claim 1, wherein the oral composition is a chewing gum, and the synergistic inhibition of the formation of plaque biofilm in the oral cavity occurs after a chewing time of at least 10 minutes.

8. The oral composition of claim 1, wherein the oral composition reduces the adherence of plaque to teeth.

9. A coated oral composition for inhibiting the formation of plaque biofilm by salivary bacteria in an oral cavity of a consumer, the coated oral composition comprising MBE and LAE in a weight ratio from about 16:1 to about 4:1 that provide a synergistic inhibition of the formation of plaque biofilm in the oral cavity.

10. The coated oral composition of claim 9, wherein the MBE comprises from about 1% to about 2% by weight of the coating.

11. The coated oral composition of claim 9, wherein the LAE comprises from about 1% to about 2% by weight of the coating.

12. The coated oral composition of claim 9, wherein the coated oral composition is selected from the group consisting of a chewing gum, a confection, a mint, a tablet, a bead, and a lozenge.

13. The coated oral composition of claim 9, wherein the coated oral composition is a chewing gum and the synergistic inhibition of the formation of plaque biofilm in the oral cavity occurs after a chewing time of at least 10 minutes.

14. A method of making a coated oral composition, the method comprising:
pretreating MBE and LAE to form a preblend mixture;
adding the preblend mixture to a coating syrup; and,
applying the coating syrup to an oral composition to produce the coated oral composition,
wherein the coated oral composition comprises MBE and LAE in amounts that provide a synergistic inhibition of the formation of plaque biofilm by salivary bacteria in an oral cavity of a consumer.

15. The method of claim 14, wherein the oral composition is selected from the group consisting of a chewing gum, a confection, a mint, a tablet, a bead, and a lozenge.

16. The method of claim 14, wherein the MBE and LAE are pretreated by blending the MBE and LAE with one or more organoleptic components.

17. The method of claim 14, wherein the MBE and LAE are pretreated by sieving the MBE and LAE.

18. The method of claim 14, wherein the weight ratio of MBE to LAE in the preblend mixture is from about 16:1 to about 8:1.

19. The method of claim 14, wherein the MBE comprises from about 1% to about 2% by weight of the coating.

20. The method of claim 14, wherein the LAE comprises from about 1% to about 2% by weight of the coating.

21. The method of claim 14, wherein the coated oral composition is a coated chewing gum.

22. The method of claim 14, wherein the MBE and LAE are pretreated by blending the MBE and LAE with a powdered gum base.

23. The method of claim 14, wherein the MBE and LAE are pretreated by pre-dissolving the MBE and LAE in a flavoring agent, glycerol, MCT oil, or combinations thereof.

24. The method of claim 14, wherein the weight ratio of MBE to LAE in the preblend mixture is from about 16:1 to about 4:1.

25. The method of claim 14, wherein the weight ratio of MBE to LAE in the preblend mixture is from about 8:1 to about 4:1.

26. The method of claim 14, wherein the weight ratio of MBE to LAE in the preblend mixture is from about 16:1 to about 8:1.

* * * * *